US011351348B2

(12) United States Patent
Kobayashi et al.

(10) Patent No.: US 11,351,348 B2
(45) Date of Patent: Jun. 7, 2022

(54) MICRONEEDLE PATCH

(71) Applicant: MEDRX CO., LTD, Higashikagawa (JP)

(72) Inventors: Katsunori Kobayashi, Higashikagawa (JP); Hidetoshi Hamamoto, Higashikagawa (JP)

(73) Assignee: MEDRX CO., LTD., Kagawa (JP)

( * ) Notice: Subject to any disclaimer, the term of this patent is extended or adjusted under 35 U.S.C. 154(b) by 65 days.

(21) Appl. No.: 16/469,137

(22) PCT Filed: Dec. 11, 2017

(86) PCT No.: PCT/JP2017/044408
§ 371 (c)(1),
(2) Date: Jun. 12, 2019

(87) PCT Pub. No.: WO2018/110510
PCT Pub. Date: Jun. 21, 2018

(65) Prior Publication Data

US 2020/0101274 A1 Apr. 2, 2020

(30) Foreign Application Priority Data

Dec. 12, 2016 (JP) ............................ JP2016-240336

(51) Int. Cl.
*A61M 37/00* (2006.01)

(52) U.S. Cl.
CPC . *A61M 37/0015* (2013.01); *A61M 2037/0023* (2013.01); *A61M 2037/0053* (2013.01); *A61M 2037/0061* (2013.01)

(58) Field of Classification Search
CPC ...... A61M 37/0015; A61M 2037/0023; A61M 2037/0053; A61M 2037/0061; A61F 13/02
See application file for complete search history.

(56) References Cited

U.S. PATENT DOCUMENTS 6,656,147 B1 12/2003 Gertsek et al.
6,743,211 B1 * 6/2004 Prausnitz ........... A61B 5/14514 604/239

(Continued)

FOREIGN PATENT DOCUMENTS

JP 2004-503341 A 2/2004
JP 2005-521527 A 7/2005

(Continued)

OTHER PUBLICATIONS

Steer, Questions from Practice: Caring for Sore Skin Around a Wound, 2011, The Pharmaceutical Journal, vol. 286, p. 661 available at https://www.pharmaceutical-journal.com/cpd-and-learning/learning-article/questions-from-practice-caring-for-sore-skin-around-a-wound/11078117.article (accessed Feb. 18, 2021) (Year: 2011).*

(Continued)

*Primary Examiner* — Amber R Stiles
(74) *Attorney, Agent, or Firm* — Morgan, Lewis & Bockius LLP

(57) ABSTRACT

Provided are a method of applying a microneedle array, and a patch or an assistant tool used therefor. When skin is to be stretched and punctured with microneedles, the microneedle array can be prevented from detaching from the skin by providing adhesive layers, with the microneedle array therebetween, in a direction different from the direction in which the skin is stretched. Additionally, the application method can be appropriately implemented by producing a patch or an assistant tool having a rigid flat plate. As a result, the microneedle array can be punctured more accurately with less stress.

16 Claims, 12 Drawing Sheets

(56) References Cited

U.S. PATENT DOCUMENTS

| | | | | |
|---|---|---|---|---|
| 2002/0128599 | A1* | 9/2002 | Cormier | A61K 9/0021 604/116 |
| 2003/0187394 | A1* | 10/2003 | Wilkinson | A61M 5/14248 604/131 |
| 2008/0183144 | A1 | 7/2008 | Trautman et al. | |
| 2009/0198189 | A1 | 8/2009 | Simons et al. | |
| 2016/0354589 | A1 | 12/2016 | Kobayashi et al. | |
| 2017/0087346 | A1 | 3/2017 | Kato et al. | |

FOREIGN PATENT DOCUMENTS

| | | | |
|---|---|---|---|
| JP | 2009-273872 | A | 11/2009 |
| JP | 2010-516337 | A | 5/2010 |
| JP | 2014-042788 | A | 3/2014 |
| WO | WO 2012/128363 | A1 | 9/2012 |
| WO | WO 2015/194260 | A1 | 12/2015 |
| WO | WO 2016/129184 | A1 | 8/2016 |

OTHER PUBLICATIONS

International Search Report received in International Patent Application No. PCT/JP2017/044408 dated Dec. 11, 2017.

* cited by examiner

[Fig.1]
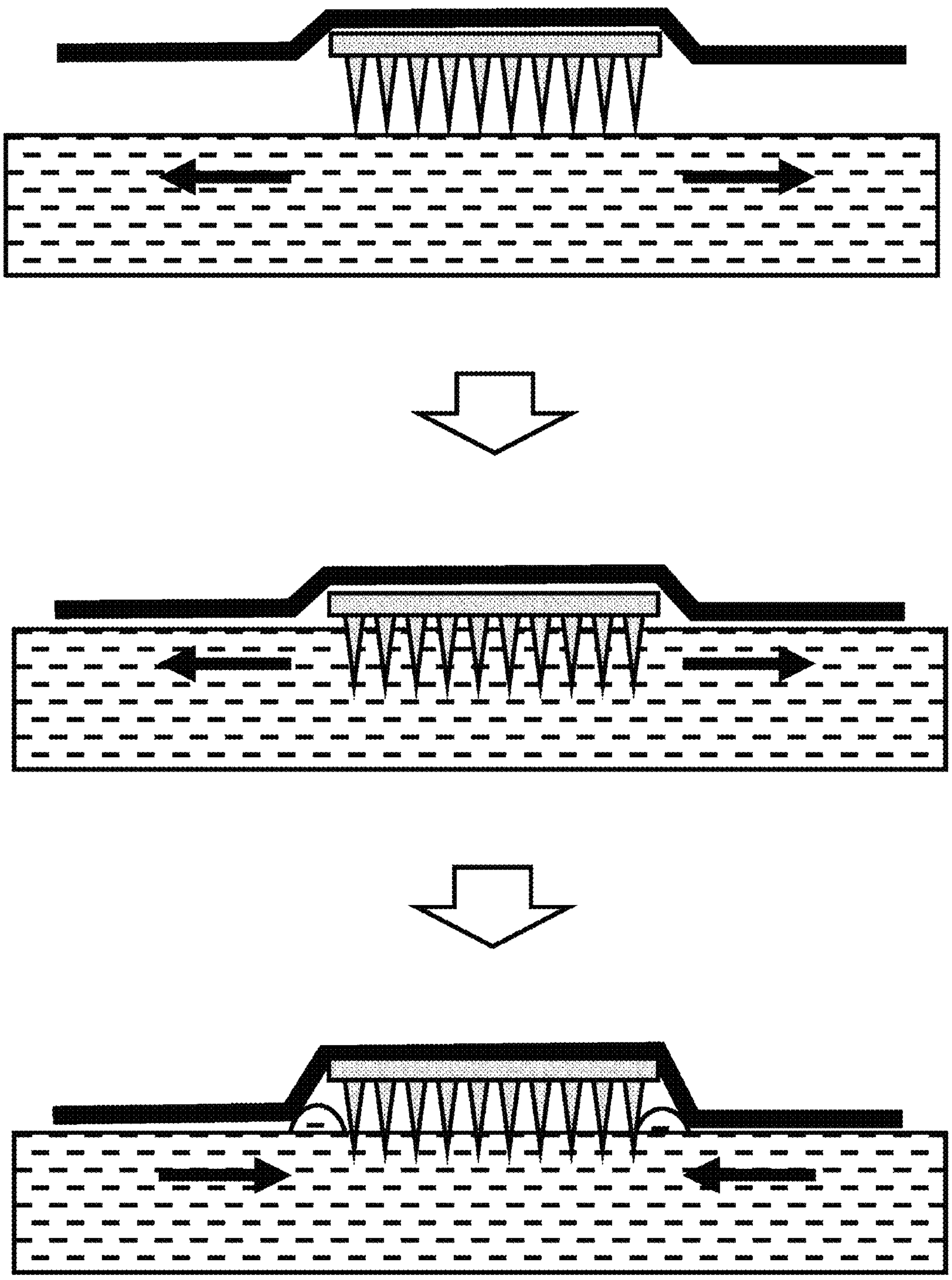

[Fig.2]
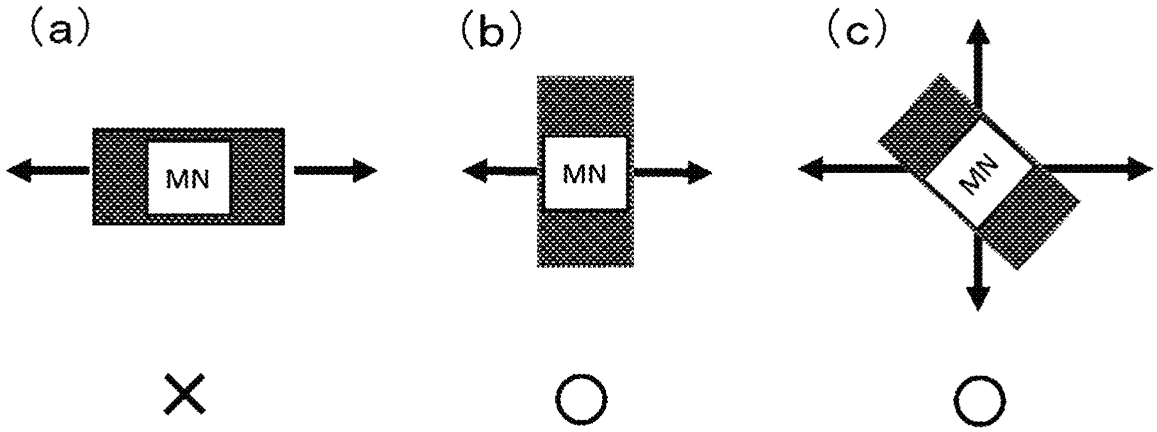
[Fig.3]
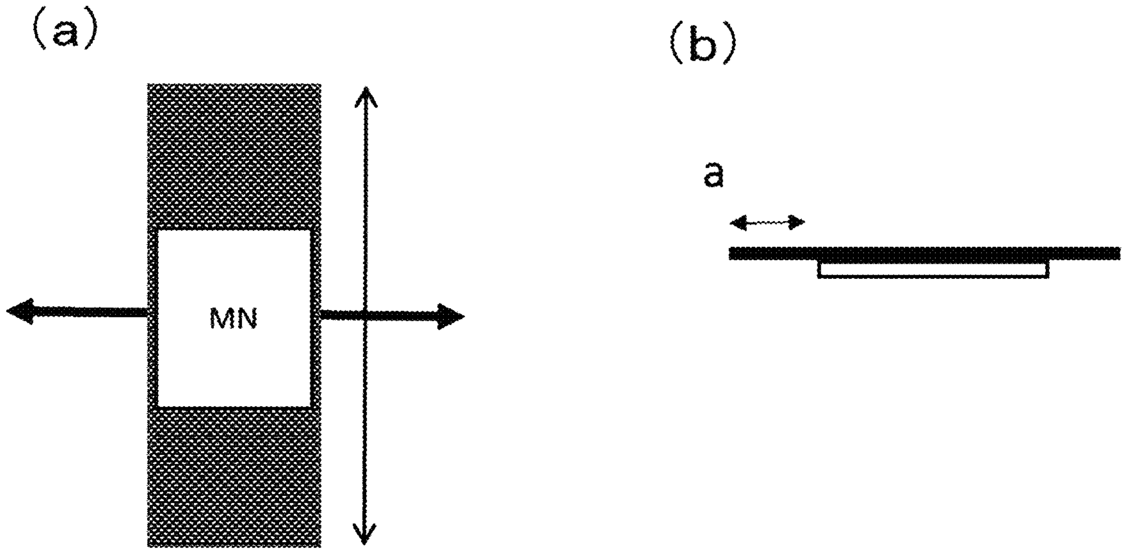
[Fig.4]
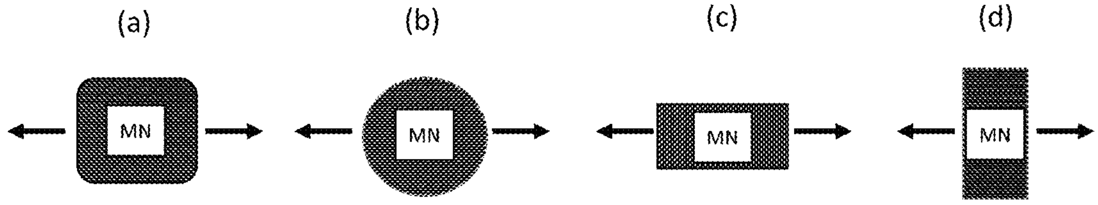

[Fig.5]
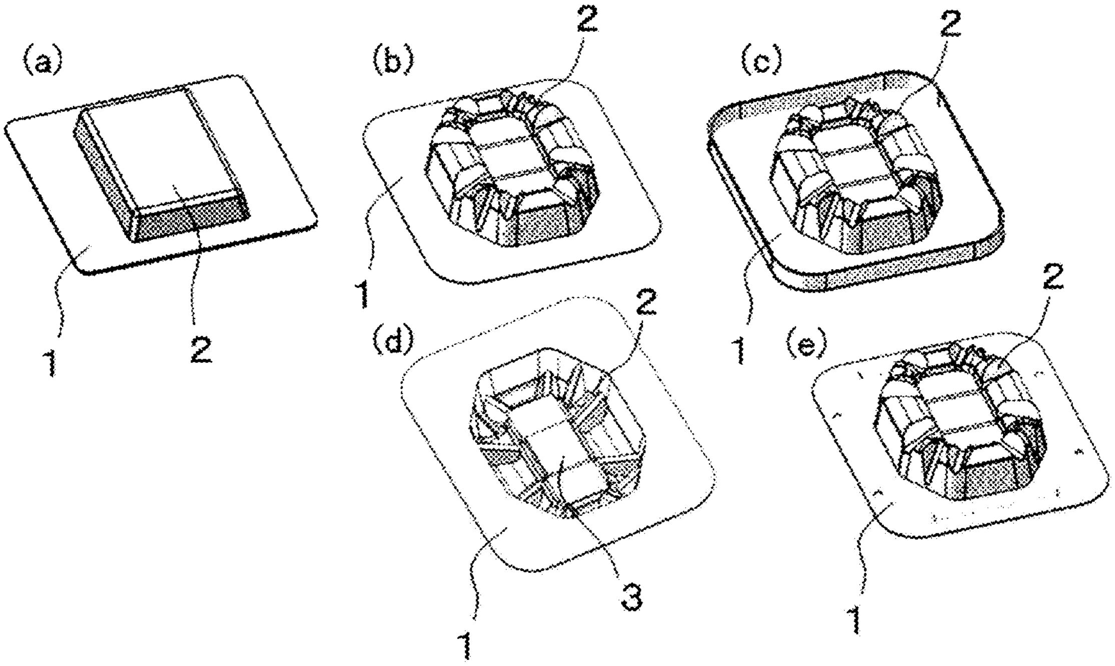
[Fig.6]
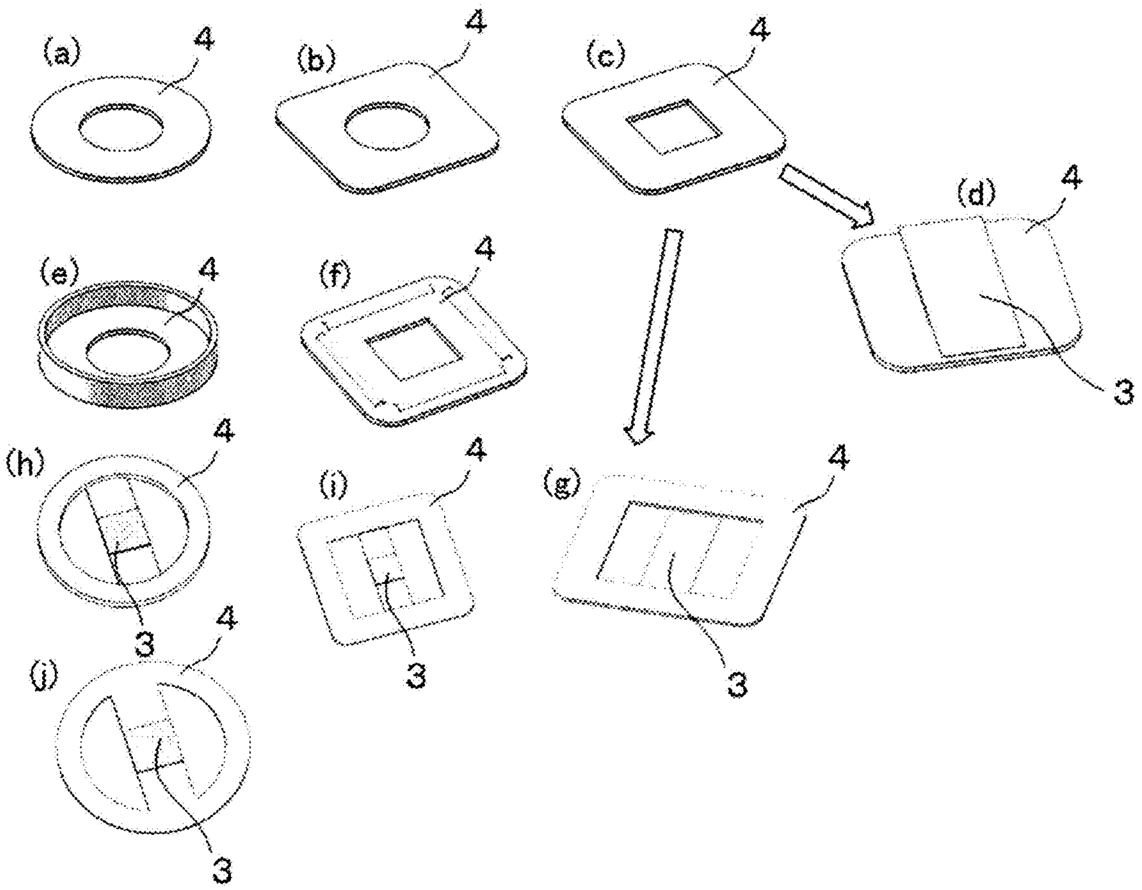

[Fig.7]
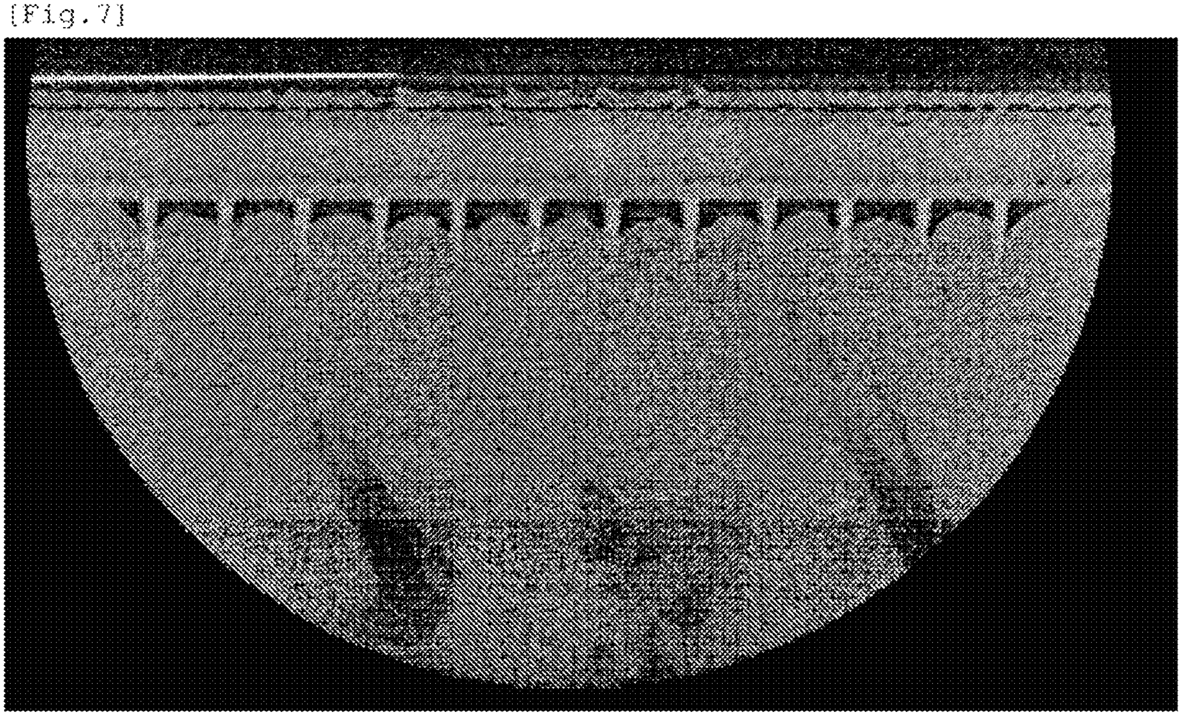

[Fig.8]
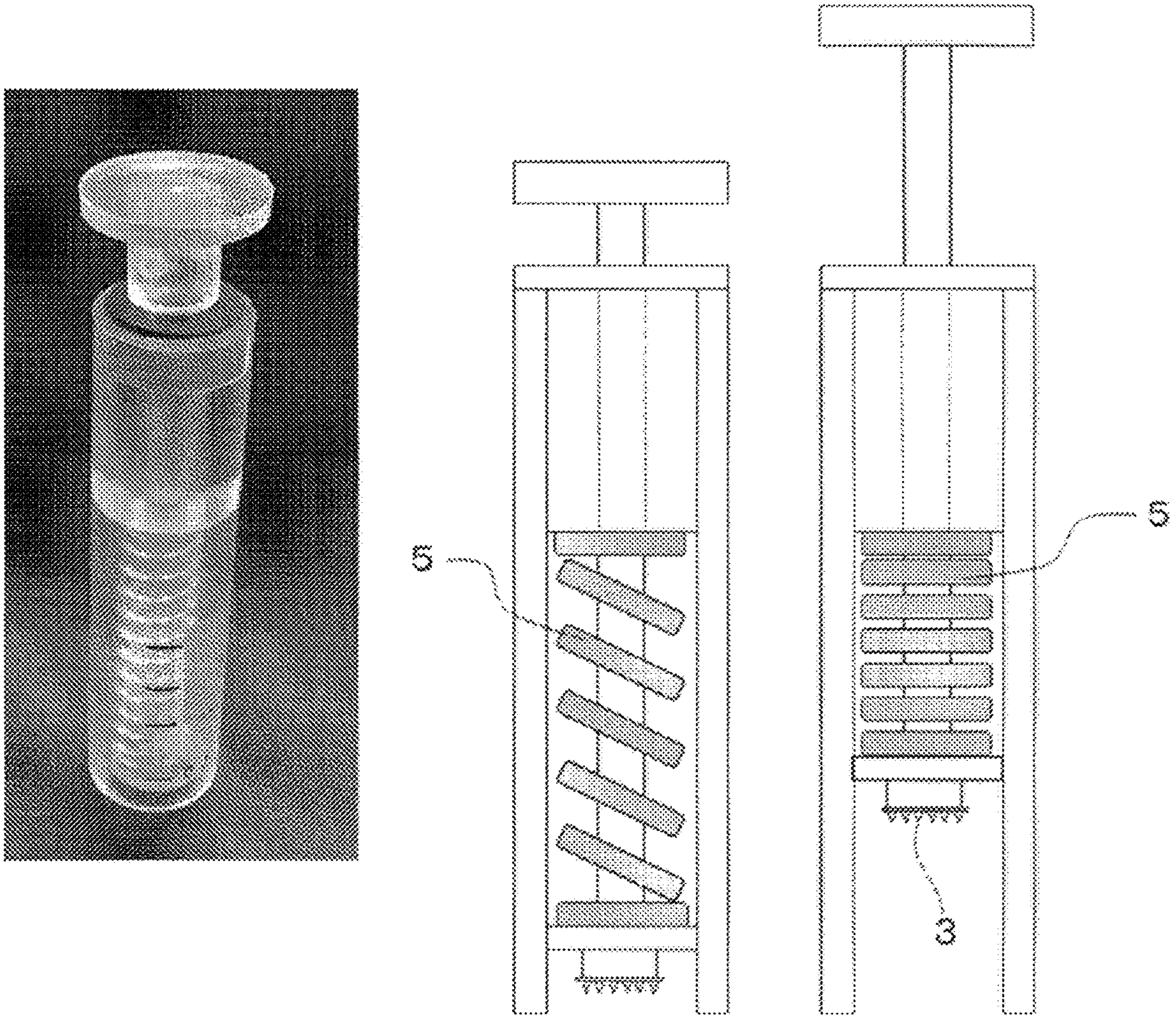

[Fig.9]
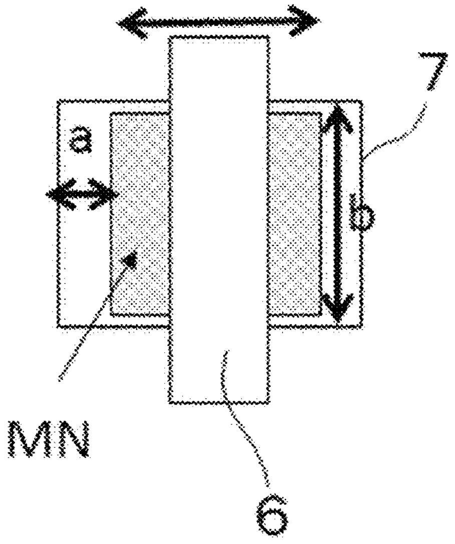
[Fig.10]
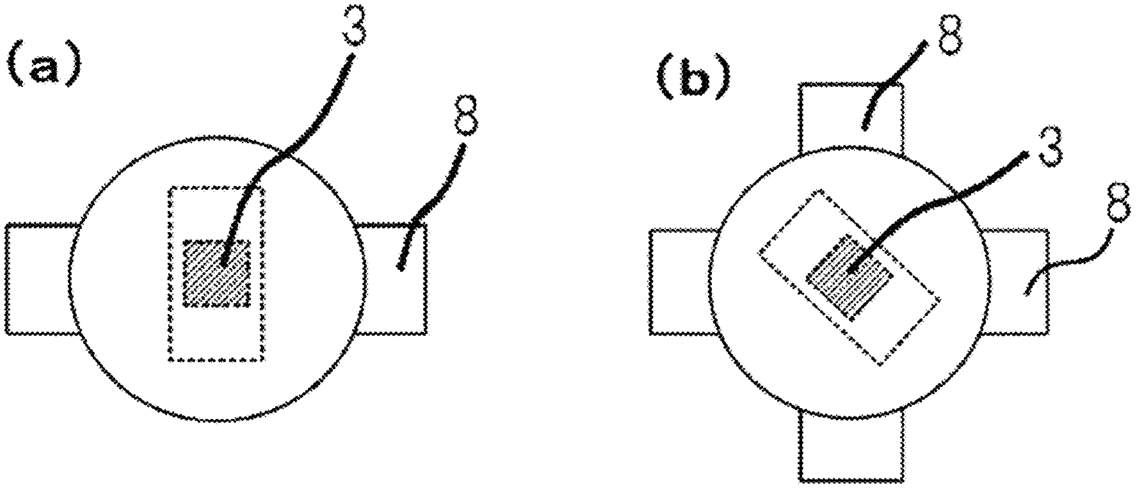

[Fig.11]
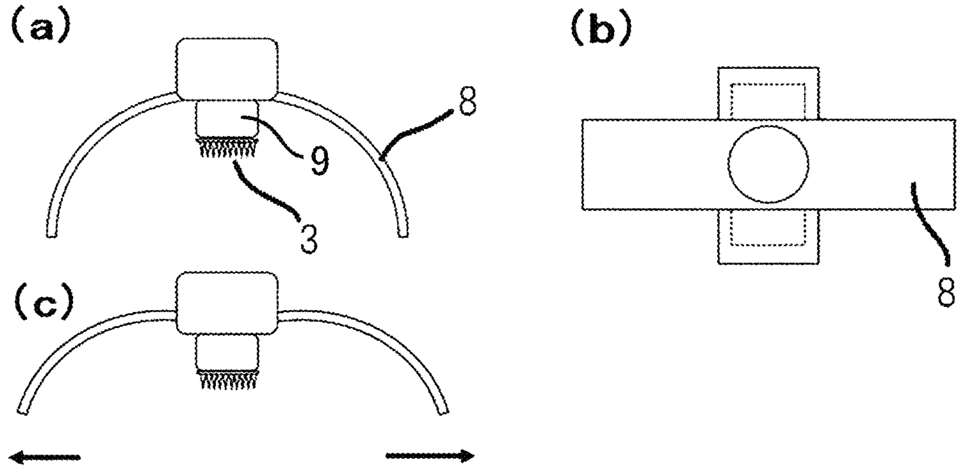
[Fig.12]
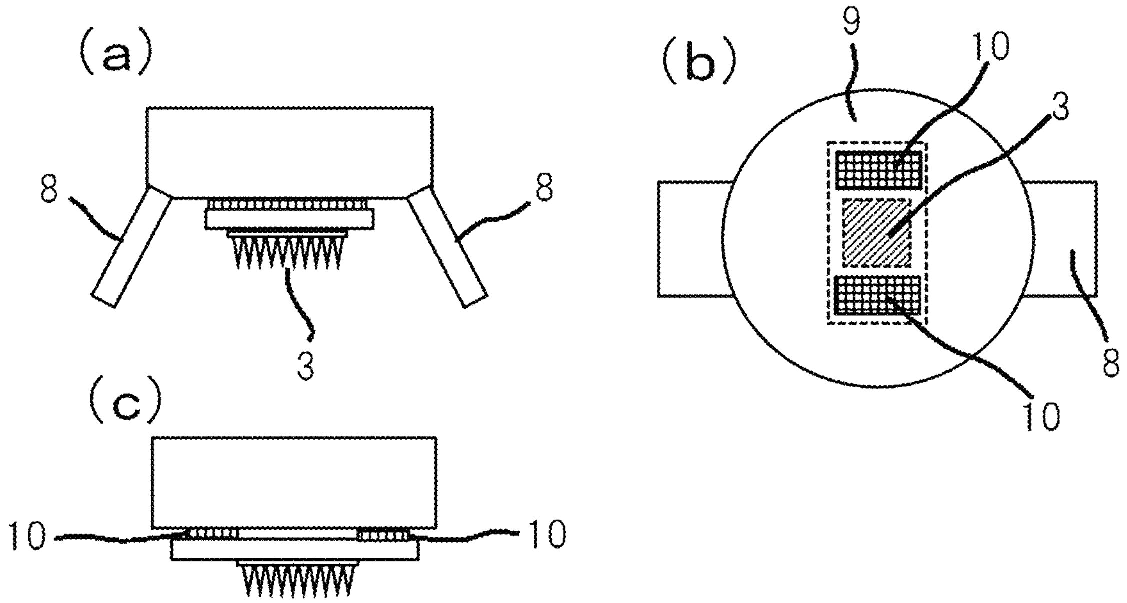

[Fig.13]
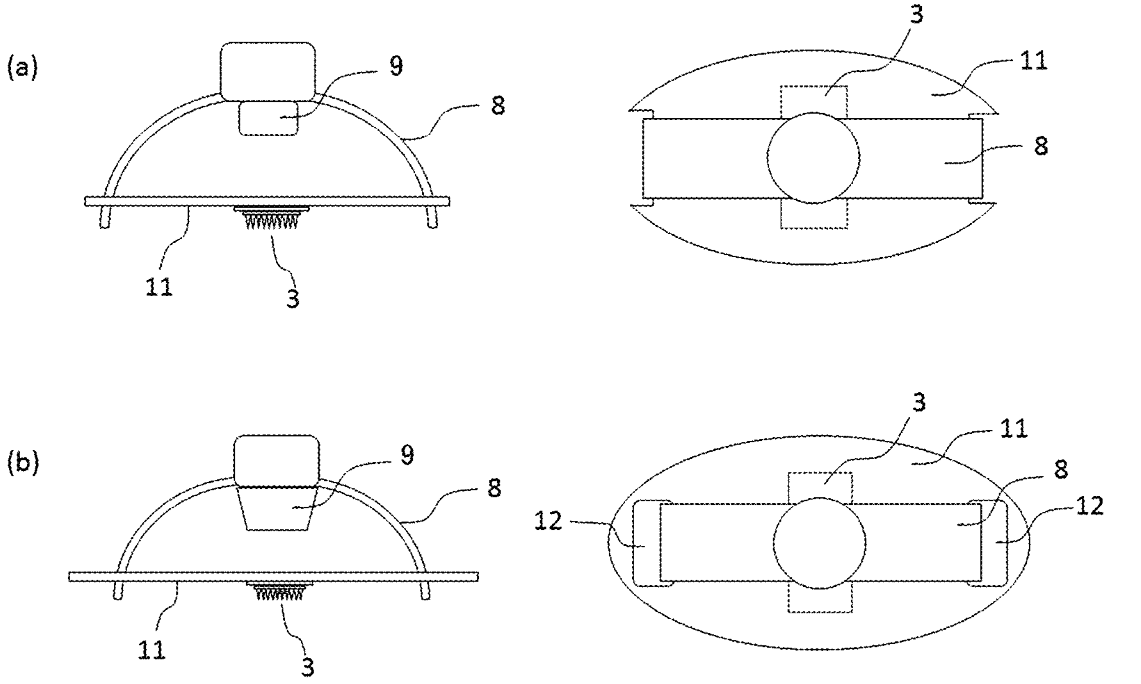
[Fig.14]
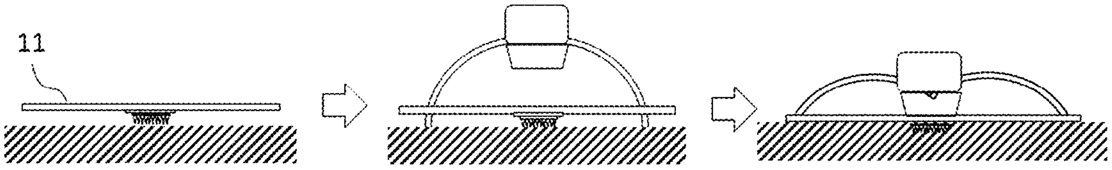
[Fig.15]
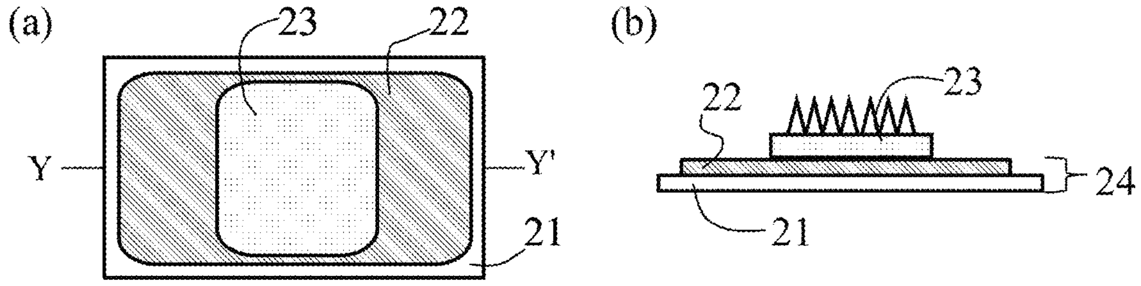

[Fig.16]
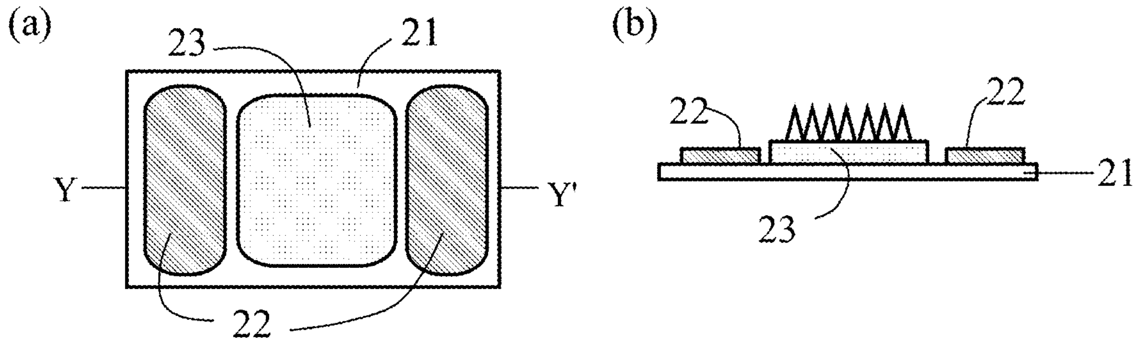
[Fig.17]
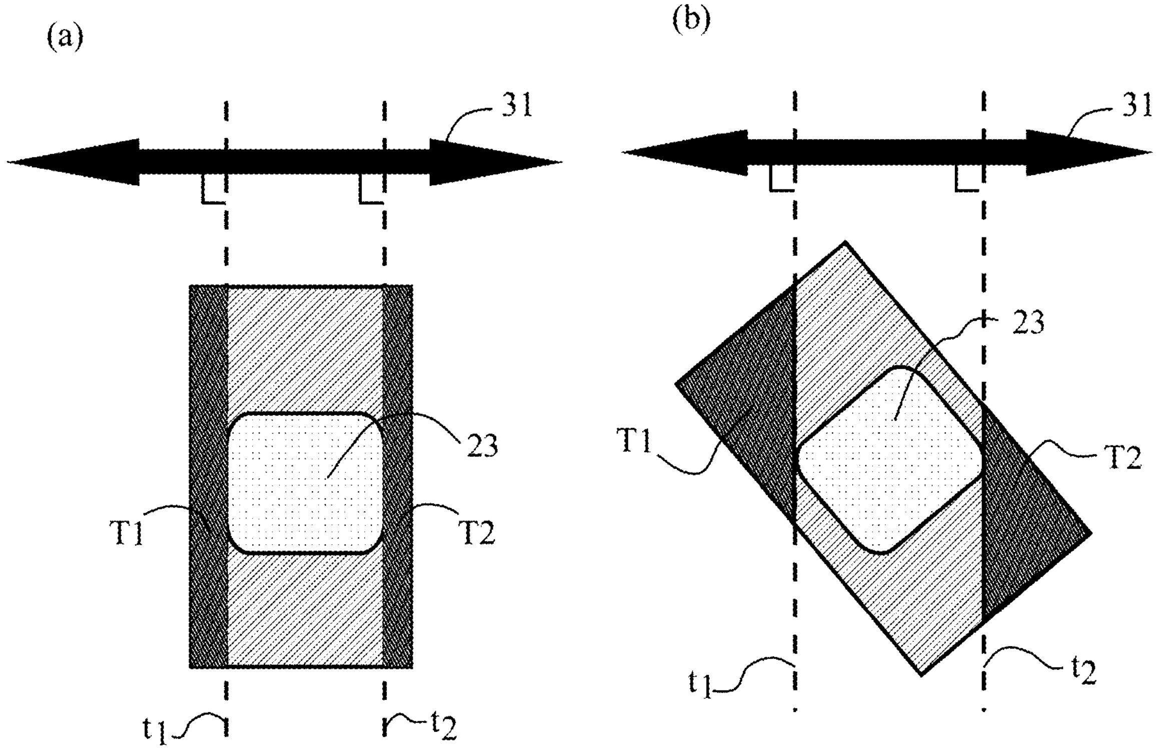

[Fig.18]
(a)
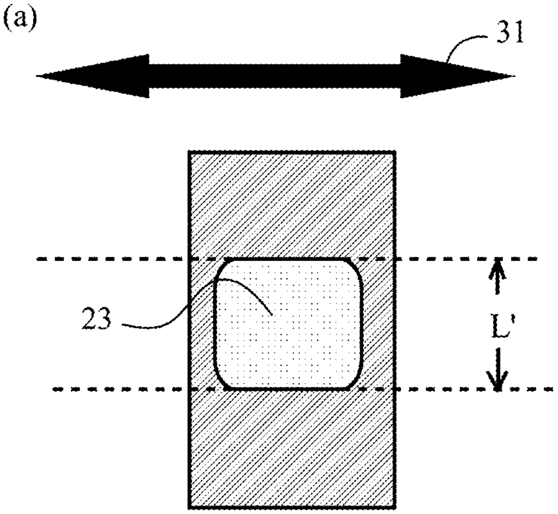
(b)
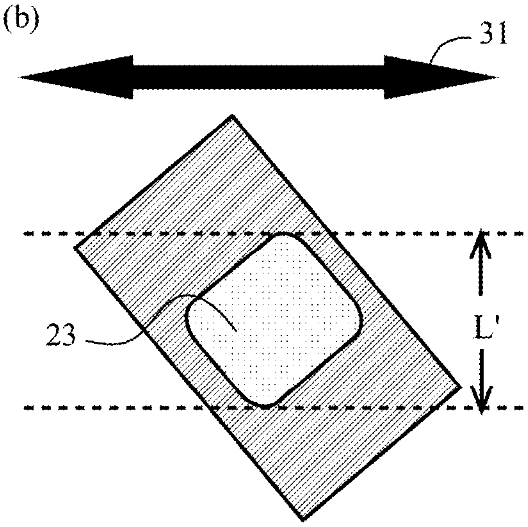
[Fig.19]
(a)
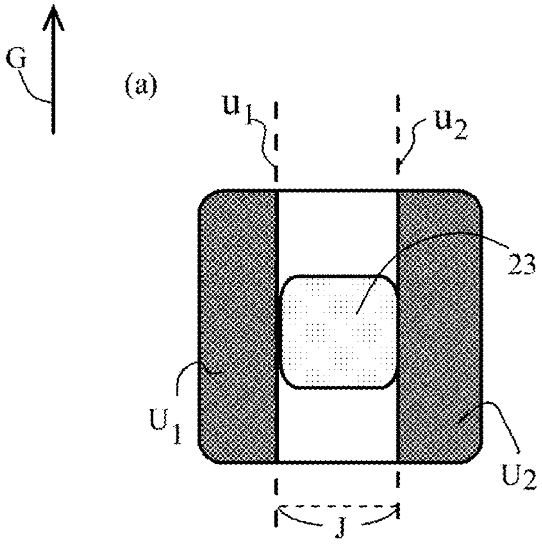
(b)
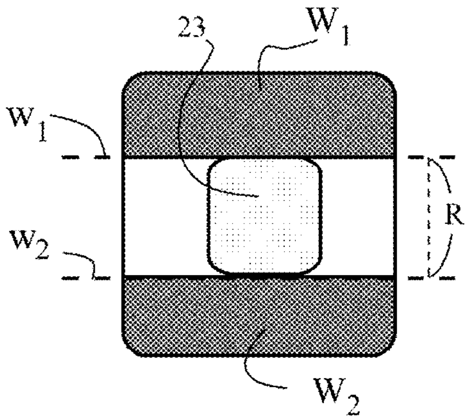

[Fig.20]
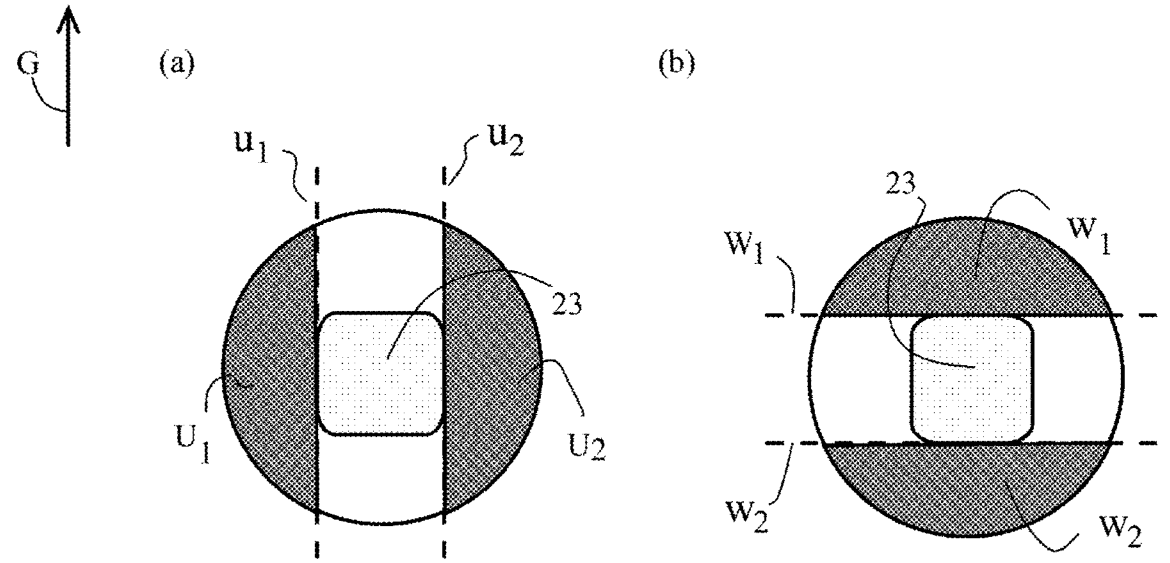
[Fig.21]
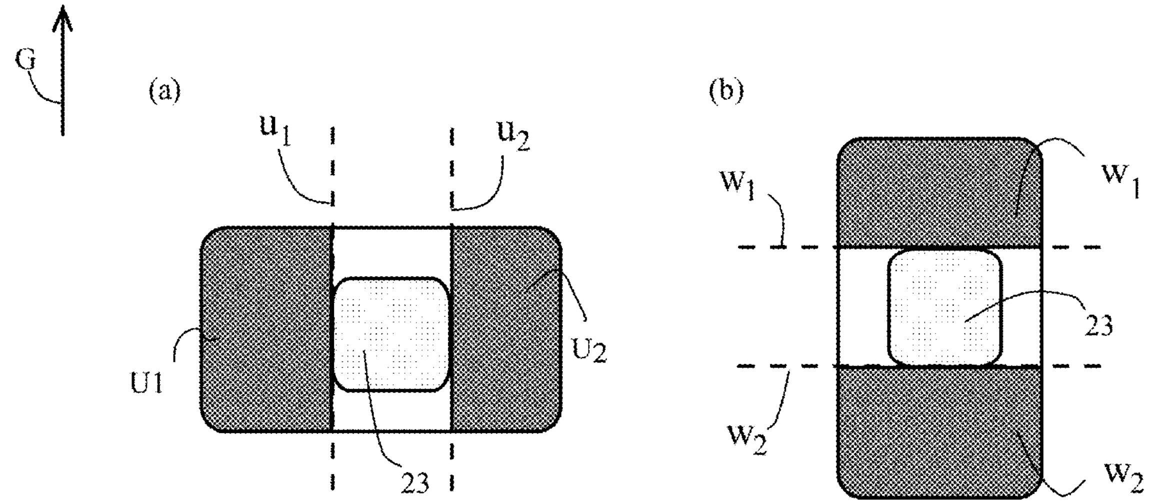

[Fig.22]
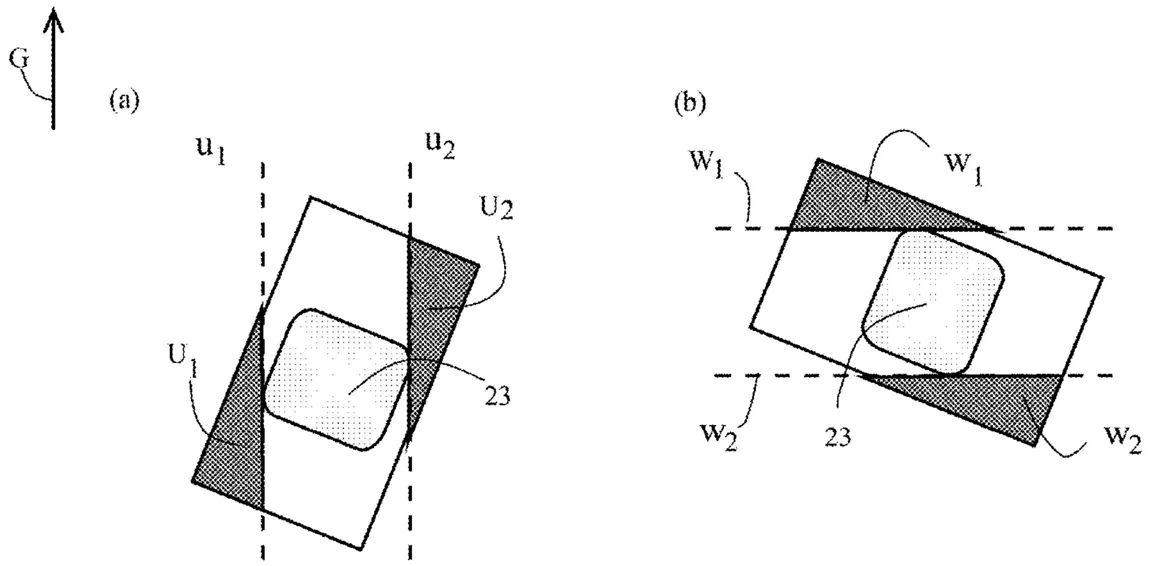

MICRONEEDLE PATCH

FIELD OF THE INVENTION

The present invention relates to a patch carrying a microneedle array. Particularly, the present invention relates to the patch which has an excellent fixing property to the skin and a method of applying the patch.

BACKGROUND ART

Percutaneous administration of a drug using the microneedle array is a field which has been actively studied in recent years. Many business firms have been examining practical manufacturing methods of the microneedle array (Patent documents 1 and 2). Moreover, with regard to a method of applying the microneedle array on the skin, methods using various types of devices have been examined (Patent documents 3 and 4).

However, there is a problem that the microneedle array applied on and puncturing the skin is detached from the skin due to the repulsive force of the skin so that a sufficient injection effect of the drug cannot be obtained. Particularly, when the skin is stretched by applying a tension in applying the microneedle array in order to improve skin-puncturing performance, the skin remarkably contracts, whereby the microneedle array is lifted up.

PRIOR ART LITERATURES

Patent Literature

Patent document 1: JP 2009-273872, A
Patent document 2: WO 2012/128363, A
Patent document 3: JP 2010-516337, A
Patent document 4: JP 2014-042788, A

SUMMARY OF THE INVENTION

Problem to be Solved by the Invention

When the microneedle array is applied while stretching the skin with the tension as described above, there has been a problem that the microneedle or the microneedle array (hereinafter, they are also referred to simply as a "microneedle array") is detached by contraction of the skin. Thus, development of a new microneedle patch which can stably maintain fixation of the microneedle array to the skin and a method of applying it has been in demand.

A main object of the present invention is to provide, for a patch carrying a microneedle array, a new patch having an excellent fixing property to the skin and a method of applying it.

Means for Solving Problem

In order to solve the aforementioned problem, the inventors examined a material of a patch portion and also examined a shape of an adhesive layer and an applying method.

First, if the microneedle array is applied after stretching the skin for improving puncturing performance of the microneedle, the microneedle is detached due to relaxation of the skin after the puncturing as illustrated in FIG. 1. Thus, the inventors have examined an appropriate applying method of a patch carrying the microneedle array. As a result, with regard to the patch of the microneedle array to be applied by stretching the skin, the inventors found that, if the patch is applied so that an adhesive force does not substantially work in a direction of stretching the skin, the object of the present invention can be achieved. For example, as illustrated in FIGS. 2(*a*) and 2(*b*), when the skin is stretched in a lateral direction, the patch is preferably applied such that there is hardly an adhesive layer on both ends of the microneedle array in the lateral direction, and wide adhesive layers are aligned above and below the microneedle array in a vertical direction as in FIG. 2(*b*). Moreover, as in FIG. 2(*c*), when the skin is stretched in two directions, that is, in the lateral and vertical directions, the patch is preferably applied such that wide adhesive layers with sandwiching the microneedle array are aligned in an intermediate direction different from the stretching directions. Thus, the inventors found that the object of the present invention can be achieved by applying such that the wide adhesive layers or the adhesive layers having a sufficient adhesive force with sandwiching the microneedle array are aligned in a direction different from the stretching directions, while the skin can be stretched in any direction.

Therefore, the present invention can comprise a method of applying a patch carrying a microneedle array, characterized by applying the patch so that the adhesive force of the patch does not substantially work in the direction in which the skin is stretched.

Moreover, the inventors have found that it is preferable that an adhesive layer of the patch used in the applying method of the present invention is not located on both end portions of the microneedle array in the direction in which the skin is stretched, or even if there is the adhesive layer on the both end portions, the adhesive layer does not have a substantial adhesive force to the skin or the adhesive layer satisfies a relationship in the following Formula (1):

$$S \times F < 1.85L \qquad \text{Formula (1)}$$

(in the Formula, S denotes an area ($cm^2$) of an adhesive layer on the patch sandwiched by an outer peripheral tangent of the microneedle array orthogonal to an axis in which the skin is stretched and an outer periphery of the patch, and if a plurality of such areas is present, it expresses each area. F denotes an adhesive force (N/cm) per unit of the adhesive layer in the direction in which the skin is stretched. L denotes an axial distance (cm) on the dimension of the microneedle array orthogonal to the direction in which the skin is stretched.)

By preparing the patch satisfying the relationship in the aforementioned formula (1), when the skin is stretched by a device or when the skin is stretched by hand without using a device, the patch of the microneedle is not detached after the application but the microneedle is inserted into the skin and fixed.

Moreover, the inventors found that, by adhering and fixing the skin with a flat plate made of a rigid resin or metal which comprises a pressure-sensitive adhesive surface and is not expanded/contracted or deformed, the detachment of the applied microneedle array can be prevented. Furthermore, with regard to this flat plate, the inventors found that a portion carrying the microneedle array may have a hole, and the object can be achieved also by pressure-applying the microneedle array to the skin through the hole for application. That is, the inventors found that, by attaching a rigid flat-plate shaped material to the stretched skin so as to prevent contraction or flaccidity of the skin, the detachment of the microneedle array can be suppressed. In addition, the inventors found that the object of the present invention can also be achieved by a patch with such a shape that the skin around a punctured portion in the stretched skin is fixed by a rigid flat plate, and the microneedle array is applied to a portion of the skin corresponding to an opening on the flat plate.

The inventors have completed the present invention on the basis of the aforementioned findings. The summary of the present invention is as follows:

[1] A method of applying a microneedle patch characterized in that the patch is applied such that an adhesive force of the patch does not substantially work in a direction in which the skin is stretched.

[2] The method of applying a microneedle patch described in the aforementioned [1], in which the application such that the adhesive force of the patch does not work is to apply the microneedle patch so that:

a) an adhesive layer is not present on both end portions of the microneedle in the direction in which the skin is stretched, or even if there are the adhesive layers on the both end portions, the adhesive layers on the both end portions have no adhesive force strong enough to be fixed to the skin; and b) the adhesive layers having the adhesive force strong enough to be fixed to the skin are applied so as to be aligned in a direction different from the direction in which the skin is stretched with sandwiching the microneedle array.

[3] The method of applying a microneedle patch described in the aforementioned [2], in which having no adhesive force strong enough to be fixed to the skin is to satisfy a relationship in the following Formula (1):

$$S \times F < 1.85L \quad \text{Formula (1)}$$

(in the Formula, S denotes an area ($cm^2$) of an adhesive layer on the patch sandwiched by an outer peripheral tangent of the microneedle array orthogonal to an axis in which the skin is stretched and an outer periphery of the patch, and if a plurality of such areas is present, it expresses each area. F denotes an adhesive force (N/cm) per unit of the adhesive layer in the direction in which the skin is stretched. L denotes an axial distance (cm) on the dimension of the microneedle array orthogonal to the direction in which the skin is stretched.)

[4] The method of applying a microneedle patch described in any one of the aforementioned [1] to [3], in which a planar shape of at least one of the patch, the adhesive layer and the microneedle array is a polygon, a tetragon, a circle or an oval.

[5] The method of applying a microneedle patch described in the aforementioned [4], in which the planar shapes of the adhesive layer and the microneedle array are a tetragon, and the Formula (1) is the following Formula (2):

$$(a \times b) \times F < 1.85L \quad \text{Formula (2)}$$

(in the Formula, a denotes a distance (cm) on the adhesive layer between an outer periphery of the microneedle array orthogonal to the direction in which the skin is stretched and an outer periphery of the adhesive layer, and b denotes an axial distance (cm) orthogonal to the direction of a. F denotes an adhesive force (N/cm) per unit of the adhesive layer in the direction in which the skin is stretched. L denotes an axial distance (cm) on the dimension of the microneedle array orthogonal to the direction in which the skin is stretched.)

[6] A microneedle patch applied to the skin by stretching and puncturing the skin with a microneedle, in which:

a) the microneedle patch comprises adhesive layers set up in a direction different from directions in which the skin is stretched with sandwiching the microneedle array; and b) there is no adhesive layer on both end portions of the microneedle array in the direction in which the skin is stretched, or even if there is an adhesive layer on the both end portion, a relationship in the following Formula (1) is satisfied:

$$S \times F < 1.85L \quad \text{Formula (1)}$$

(in the Formula, S denotes an area ($cm^2$) of an adhesive layer on the patch sandwiched by an outer peripheral tangent of the microneedle array orthogonal to an axis in which the skin is stretched and an outer periphery of the patch, and if a plurality of such areas is present, it expresses each area. F denotes an adhesive force (N/cm) per unit of the adhesive layer in the direction in which the skin is stretched. L denotes an axial distance (cm) on the dimension of the microneedle array orthogonal to the direction in which the skin is stretched.)

[7] The microneedle patch described in the aforementioned [6], in which a planar shape of at least one of the patch, the adhesive layer and the microneedle array is a polygon, a tetragon, a circle or an oval.

[8] The microneedle patch described in the aforementioned [7], in which the planar shapes of the adhesive layer and the microneedle array are a tetragon, and the Formula (1) is the following Formula (2):

$$(a \times b) \times F < 1.85L \quad \text{Formula (2)}$$

(in the Formula, a denotes a distance (cm) on the adhesive layer between an outer periphery of the microneedle array orthogonal to the direction in which the skin is stretched and an outer periphery of the adhesive layer, and b denotes an axial distance (cm) orthogonal to the direction of a. F denotes an adhesive force (N/cm) per unit of the adhesive layer in the direction in which the skin is stretched. L denotes an axial distance (cm) on the dimension of the microneedle array orthogonal to the direction in which the skin is stretched.)

[9] A microneedle patch applied to the skin by stretching and puncturing the skin with a microneedle, in which:

a) the microneedle patch comprises adhesive layers set up in a direction different from directions in which the skin is stretched with sandwiching the microneedle array;

b) a holding time related to a holding force of the adhesive layer on the patch sandwiched by an outer peripheral tangent of the microneedle array in parallel with an axis in which the skin is stretched and an outer periphery of the patch is 100 seconds or more;

c) if there is an adhesive layer on both end portions of the microneedle array in the direction in which the skin is stretched, a holding time related to a holding force of the adhesive layer sandwiched by the outer peripheral tangent of the microneedle array orthogonal to the axis in which the skin is stretched and the outer periphery of the patch is less than 120 seconds; and d) in the b) and c), if the sandwiched adhesive layers are present at a plurality of places, a holding time related to a holding force of each of the adhesive layers is respectively 100 seconds or more and less than 120 seconds.

[10] The microneedle patch described in the aforementioned [9], in which the holding time related to the holding force of the adhesive layer sandwiched by the outer peripheral tangent of the microneedle array in parallel with the axis in which the skin is stretched and the outer periphery of the patch is 120 seconds or more.

[11] The microneedle patch described in the aforementioned [9] or [10], in which the holding time related to the holding force of the adhesive layer sandwiched by the outer peripheral tangent of the microneedle array orthogonal to the axis in which the skin is stretched and the outer periphery of the patch is 100 seconds or less.

[12] A patch including a microneedle array for applying a microneedle by stretching and puncturing the skin with the microneedle, in which:

a) the patch comprises a rigid flat plate on which a pressure-sensitive adhesive is set up; and b) the microneedle array is set up on the rigid flat plate, or b') the rigid flat plate is raised at a center part to become hollow, and the microneedle array is set up on a plane at the center part of the hollow portion.

[13] The patch described in the aforementioned [12], in which a top surface and/or a side surface of the hollow portion is deformed so that the microneedle array is transferable to the skin side.

[14] The patch described in the aforementioned [12] or [13], in which the top surface and/or the side surface has a fold or an edge for promoting deformation.

[15] An assistant tool for applying a microneedle by stretching and puncturing the skin with the microneedle, in which:

a) the assistant tool comprises a rigid flat plate on which a pressure-sensitive adhesive is set up;

b) the rigid flat plate has a ring shape with an opening portion at a center; and c) a size of the opening portion is a size which does not hinder passage of the microneedle array.

[16] The assistant tool described in the aforementioned [15], in which the rigid flat plate is made up of a rigid resin.

[17] A device for a microneedle array comprising: a microneedle patch described in any one of the aforementioned [6] to [14]; and an applicator for stretching the skin and transferring/applying the microneedle array to the skin.

[19] A method of applying a microneedle patch comprising: a process (A) of stretching the skin; a process (B) of applying the microneedle patch on the stretched skin surface; and a process (C) of releasing the stretching of the skin, in which an adhesive force of an adhesive layer satisfies the following Formula (1') in a relationship with a stretching axis in the process (A):

$$S' \times F' < 1.85L' \quad \text{Formula (1')}$$

(in the Formula, S denotes an area ($cm^2$) of a section T not including the microneedle array in the adhesive layer defined by an outer peripheral tangent t of the microneedle array at a right angle to a stretching axis. F denotes an adhesive force (N/cm) per unit of the adhesive layer of the section T. L' denotes a length (cm) in a direction at a right angle to the stretching axis of the microneedle array.)

[20] A microneedle patch satisfying the following Formula (3) and/or (4):

$$P \times Q < 1.85R \quad \text{Formula (3)}$$

(in the Formula, P denotes an area ($cm^2$) of a section U not including the microneedle array in the adhesive layer defined by an outer peripheral tangent u of the microneedle array. Here, the aforementioned outer peripheral tangent u is in parallel with a main axis. Q denotes an adhesive force (N/cm) per unit of the adhesive layer in the section U. R denotes a length of the microneedle array in the main axis direction.)

$$H \times I > 1.85J \quad \text{Formula (4)}$$

(in the Formula, H denotes an area ($cm^2$) of a section W not including the microneedle array in the adhesive layer defined by an outer peripheral tangent w of the microneedle array. Here, the outer peripheral target w is perpendicular to a main axis. I denotes an adhesive force (N/cm) per unit of the section W. J denotes a length in a direction perpendicular to the main axis.)

[21] The microneedle patch described in the aforementioned [20], satisfying both the Formula (3) and the Formula (4).

[22] A microneedle patch, in which a holding time related to a holding force of an adhesive layer in a section U not including a microneedle array in the adhesive layer defined by an outer peripheral tangent u of the microneedle array in parallel with a main axis is 120 seconds or less.

[23] A microneedle patch, in which a holding time related to a holding force of an adhesive layer in a section W not including a microneedle array in the adhesive layer defined by an outer peripheral tangent w perpendicular to a main axis is 100 seconds or less.

[24] A microneedle patch, in which a holding time related to a holding force of an adhesive layer of a section U is 120 seconds or less and a holding time related to a holding force of the adhesive layer in a section W is 100 seconds or more.

[25] The microneedle patch described in any one of the aforementioned [22] to [24] further satisfying the Formula (3) and/or (4).

Effect of the Invention

The method of applying the microneedle array according to the present invention, the microneedle patch used for the method, and the assistant tool for applying or puncturing are excellent in improving puncturing performance of the microneedle and in causing the microneedle or an array thereof to adhere to the skin.

A state of the skin to be punctured with the microneedle is largely different depending on the age. For example, stretchability and resilience of the skin become poorer as a child grows to an adult and an elder person. Thus, the puncturing performance of the microneedle is also largely influenced. According to the present invention, variation in the puncturing performance due to the resilience of the skin can be avoided while stable puncturing performance of the microneedle and quantitativity of drug administration are promoted. Alternatively, according to the present invention, the detachment of the microneedle array from the skin caused by skin contraction can be avoided. As a result, administration of a required amount of the drug carried by the microneedle array can be achieved. That is, the skin is stretched so as to improve the puncturing, the detachment of the microneedle (array) from the skin after application can be avoided, and quantitative drug administration by the microneedle can be realized.

BRIEF DESCRIPTION OF THE DRAWINGS

FIG. 1 illustrates that, when the skin is stretched and a microneedle patch is applied as it is, the skin shrinks and a microneedle array is detached. In each figure, an upper part illustrates the microneedle patch, while a lower part illustrates the skin. An upper view illustrates that a tension is applied by stretching the skin in directions of right and left arrows. A middle view illustrates that the microneedles puncture the skin and are inserted therein while the skin is kept stretched. A lower view illustrates that stretching of the skin is stopped, the skin shrinks, and the patch is also to shrink.

FIG. 2 illustrates an installation direction of the microneedle patch. In the figures, arrows indicate stretching directions of the skin. Reference character MN denotes a microneedle array. A black portion around MN indicates an adhesive layer. Circle marks and a cross mark indicate whether the microneedle array is detached or not when the stretched skin shrinks. The circle mark indicates that the microneedle array does not or hardly detachment. The cross mark indicates that the microneedle array is detached.

FIG. 3 illustrates an installation direction (a) of the microneedle patch and a sectional view (b) thereof along the stretching direction of the skin. Reference character MN denotes a microneedle array. A black portion around MN indicates the adhesive layer. In FIG. 3(*a*), right and left arrows indicate the stretching directions of the skin. A vertical bidirectional arrow indicates a length of the patch. In FIG. 3(*b*), a horizontal bidirectional arrow indicates a length a.

FIG. 4 illustrates shapes and installation directions of the microneedle patch. In the figures, arrows indicate the stretching directions of the skin. Reference character MN denotes a microneedle array. A black portion around MN indicates the adhesive layer.

FIG. 5 illustrates specific examples of the patch including the microneedle array having a rigid flat plate and a hollow center part. Figures except FIG. 5(*d*) are perspective views (projecting views) seen from a side where the hollow part is raised, and FIG. 5(*d*) is a perspective view (recessed view) seen from a recessed side.

FIG. 6 illustrates specific examples of an assistant tool for applying the microneedle array to the skin.

FIG. 7 is an X-ray micro CT photographic image (cross-sectional image) when the microneedle patch is applied to a human skin model and the skin model is punctured with the microneedle.

FIG. 8 illustrates a spring-type jig for ejecting the microneedle array to the skin with a certain pressure. The left view is a photo of the entirety, and right two views are front sectional schematic views thereof, in which the left one illustrates a state where a piston is pressed and a spring is extended, while the right one illustrates a state where the piston is pulled up for a certain distance and the spring is contracted.

FIG. 9 is a schematic view illustrating a shape of a patch used in Example 2. Reference character MN denotes a microneedle array. A horizontal bidirectional arrow on an upper part indicates the stretching direction of the skin.

FIG. 10 is planar perspective views seen from above of an example of a device of the microneedle array. FIG. 10(*a*) illustrates the one having two components for stretching the skin, and FIG. 10(*b*) illustrates the one having four components for stretching the skin.

FIG. 11 illustrates an example of the device of the microneedle array. FIG. 11(*a*) illustrates a front view, FIG. 11(*b*) illustrates a plane view, and FIG. 11(*c*) illustrates a front view when the member for stretching the skin is extended.

FIG. 12 illustrates an example of the device of the microneedle array. FIG. 12(*a*) illustrates a front view, FIG. 12(*b*) illustrates a rear view (a view from the microneedle array side), and FIG. 12(*c*) illustrates a sectional view along a vertical center line in FIG. 12(*b*), respectively.

FIG. 13 illustrates an example of the device of the microneedle array. FIG. 13(*a*) left and FIG. 13(*b*) left illustrate front views, and FIG. 13(*a*) right and FIG. 13(*b*) right illustrate plan views of each left view.

FIG. 14 illustrate schematic views of use of the device according to FIG. 13.

FIG. 15 illustrates an example of the microneedle patch.

FIG. 16 illustrates an example of the microneedle patch.

FIG. 17 is views for explaining an applying method of the present invention.

FIG. 18 is views for explaining the applying method of the present invention.

FIG. 19 illustrates an example of the microneedle patch.

FIG. 20 illustrates an example of the microneedle patch.

FIG. 21 illustrates an example of the microneedle patch.

FIG. 22 illustrates an example of the microneedle patch.

DETAILED DESCRIPTION OF THE EMBODIMENTS

In this Specification, the term "microneedle patch" is a patch in which a microneedle array is carried on a surface of a pressure-sensitive adhesive side of the patch consisting of a support and a pressure-sensitive adhesive. In the microneedle patch, a layer made of the pressure-sensitive adhesive is called an "adhesive layer" in some cases. The adhesive layer may be set up on the whole or apart of the support.

The term "microneedle device (hereinafter, referred to simply as a "device" in some cases)" is an apparatus (applicator) for puncturing the skin with the microneedle and for applying the patch, and the microneedle patch is set up in the apparatus in a state where it can be applied to the skin.

The applicator is equipped with at least a mechanism for stretching the skin with solving flaccidity of the skin, applying a tensed state to the skin, and holding the state.

In the "microneedle array" according to the present invention, 50 to 1000 pieces/$cm^2$ of the microneedles, each having a height within a range of 100 to 1000 μm, are set up. The larger the number of microneedles is, the more the drug carrying amount can be increased. A preferable height of the microneedle is within a range of 120 to 800 μm, or more preferably within a range of 150 to 600 μm.

A material of the microneedle array is not particularly limited as long as it can puncture the skin with the microneedle and can carry a drug. Examples thereof include metal, plastic, and ceramics. Moreover, the examples include stainless, iron, titanium, polyesters, polycarbonates, polystyrenes, polyolefins, acrylic resins, polycycloolefins, and silicon. Among polyesters, polyglycolic-acid based biodegradable resins, polylactic-acid based biodegradable resins and the like are preferable in view of safety since they are gradually degraded in organisms.

A tip diameter of the microneedle is usually within a range of 1 to 20 μm. In order to improve an effect of smoothly puncturing into a skin epidermal layer of a patient, the one having a tip diameter within a range of 1 to 10 μm is preferable. On the other hand, the tip diameter exceeding 30 μm is not preferable because resistance when puncturing the skin becomes larger so that it becomes hard for the microneedle to puncture the skin, and the distal end is made to be easily deformable.

A shape of the microneedle can be selected as appropriate in accordance with a purpose and includes a conical shape, a pyramid shape or even a shape in which a cone is mounted at a center of a truncated cone.

A planar shape of the microneedle array is not particularly limited but can be selected as appropriate in accordance with the purpose. Examples of a basic shape include a polygon (e.g., a tetragon, a hexagon, an octagon), a circle, and an oval, for example. A tetragon or a polygon is preferable.

A pressing force is not particularly limited as long as it can make the microneedle puncture the skin. Since the force gives a pain during pressing when it is too large, the force is preferably within a range of 1 to 200 N or more preferably within a range of 1 to 100 N. Since the pressing force is limited, a microneedle which can puncture the skin smoothly even with a small load is required. For example, it is preferable that, when the microneedle array is pushed into by 10 mm from the skin surface, 80% or more of the microneedles show puncturing performance. Moreover, it is preferable that, when it is pressed onto the skin by applying a force of 100 Newton (N) on a substrate with a diameter of 10 mm, 80% or more of the microneedle shows puncturing performance.

The microneedle (array) according to the present invention can be manufactured in accordance with conventional manufacturing methods. For example, the microneedle (array) according to the present invention can be manufactured in accordance with the manufacturing methods described in Patent application publications WO2012/057345 and WO2013/162053, for example.

The "pressure-sensitive adhesive" (an adhesive in the adhesive layer) used in the present invention only needs to be medical one, and well-known products can be used. Specifically, it includes: an acrylic adhesive made of an acrylic polymer, styrene block copolymers such as a styrene-isoprene-styrene block copolymer and styrene-butadiene-styrene block copolymer; rubber-based adhesives such as polyisoprene, polyisobutylene and polybutadiene; silicon-based adhesives such as silicon rubber, dimethylsiloxane base and diphenylsiloxane base; vinylether-based adhesives such as polyvinylmethylether, polyvinylethylether and polyvinylisobutylether; vinylester-based adhesives such as vinyl-acetate-ethylene copolymer; and polyester-based adhesives made of a carboxylic acid component such as dimethylterephthalate, dimethylisophthalate and dimethylphthalate; and a polyalcohol component such as ethylene glycol. These adhesives may be used alone or in combination of two or more.

The support constituting the patch is not particularly limited as long as it can be used for medical purposes and can include supporting bodies made of fibers, resins, and metals, for example. Examples of the support made of fiber include a non-woven cloth and a woven cloth, and examples of materials specifically include cotton, rayon, silk, pulp, and chemical fibers such as polyester, for example. Examples of the materials for the support made of resin specifically include polyethylene, polypropylene, polyvinylchloride, acrylic resin, polyethyleneterephthalate, polystyrene, acrylonitrile-butadiene-styrene copolymer, polycarbonate, polyamide, fluorine resin, polybutyleneterephthalate, urethane and the like. Examples of the materials for the support made of metal specifically include aluminum, stainless, and titanium, for example. However, the patches of the present invention in the following third embodiment are not limited thereto.

The planar shape of the microneedle patch is not particularly limited but can be selected as appropriate in accordance with the purpose. For example, examples of a basic shape include a polygon (e.g., a tetragon, a hexagon, an octagon), a circle, and an oval. A tetragon or a polygon is preferable.

The adhesive layer can be usually set up substantially on one surface of the patch but may be separated into plural parts and set up. When the adhesive layer is separated into plural parts and set up, a planar shape of each of the adhesive layers can also be selected from a polygon (e.g., a tetragon, a hexagon, an octagon), a circle, and an oval as appropriate, but a tetragon is preferable.

1. Method of Applying Microneedle Patch

A method of applying a microneedle patch according to the present invention (hereinafter, referred to as an "applying method of the present invention") is characterized by applying the patch so that an adhesive force of the patch does not substantially work in a direction in which the skin is stretched.

The phrase "the adhesive force does not work" means that a force for fixing the patch to the skin does not work. And the phrase "to apply (the patch) so that the adhesive force does not work" refers to the application such that: a) an adhesive layer is not present on both end portions of the microneedle in the direction in which the skin is stretched, or even if there are the adhesive layers on the both end portions, the adhesive layers on the both end portions do not have an adhesive force strong enough to be fixed to the skin; and b) the adhesive layers having the adhesive force strong enough to be fixed to the skin are applied so as to be aligned in a direction different from the direction in which the skin is stretched with sandwiching the microneedle array.

The phrase "does not have an adhesive force strong enough to be fixed to the skin" means that a relationship in the following Formula (1) is satisfied:

$$S \times F < 1.85L \quad \text{Formula (1)}$$

(in the Formula, S denotes an area ($cm^2$) of an adhesive layer on the patch sandwiched by an outer peripheral tangent of the microneedle array orthogonal to an axis in which the skin is stretched and an outer periphery of the patch, and if a plurality of such areas is present, it expresses each area. F denotes an adhesive force (N/cm) per unit of the adhesive layer in the direction in which the skin is stretched. L denotes an axial distance (cm) on the dimension of the microneedle array orthogonal to the direction in which the skin is stretched.)

The applying method of the present invention and the microneedle patch which can be used with the method will be described below by referring to the drawings. FIG. 15 illustrates an example of the microneedle patch which can be used with the applying method of the present invention. In FIG. 15, FIG. 15(*a*) is a plane view of the microneedle patch, and FIG. 15(*b*) is a sectional view along a Y-Y' direction of the microneedle patch illustrated in FIG. 15(*a*). In the microneedle patch, a microneedle array 23 is carried on a surface of an adhesive layer side of a patch 24 consisting of a support 21 and an adhesive layer (pressure-sensitive adhesive) 22. FIG. 16 illustrates another example of the microneedle patch which can be used with the applying method of the present invention. In FIG. 16, FIG. 16(*a*) is a plane view of the microneedle patch, and FIG. 16(*b*) is a sectional view along the Y-Y' direction of the microneedle patch illustrated in FIG. 16(*a*). The microneedle array 23 may be set up on the adhesive layer 22 as illustrated in FIG. 15 or may be set up directly on the support 21 without the adhesive layer 22.

Regardless of the shape of the patch, the relationship in the aforementioned Formula (1) is preferably satisfied.

Particularly, when the tetragon adhesive layer and microneedle array as illustrated in FIGS. 3, 4, and 17(*a*) are used, the following Formula (2) is preferably satisfied, in which S in the Formula (1) is equal to (a×b).

$$(a \times b) \times F < 1.85L \quad \text{Formula (2)}$$

(in the Formula, a denotes a distance (cm) on the adhesive layer between an outer periphery of the microneedle array orthogonal to the direction in which the skin is stretched and an outer periphery of the adhesive layer, and b denotes an axial distance (cm) orthogonal to the direction of a. F denotes an adhesive force (N/cm) per unit of the adhesive layer in the direction in which the skin is stretched. L denotes an axial distance (cm) on the dimension of the microneedle array orthogonal to the direction in which the skin is stretched.)

Examples of more preferable applying methods of the present invention include, as illustrated in FIG. 3, application of the patch in a direction perpendicular to the stretching direction of the skin. In that case, it is easy to measure a and b. Moreover, L varies depending on the shape of the microneedle array, and it indicates a diameter if the microneedle array is circular, and it indicates a length of one side if the microneedle array is rectangular as in FIGS. 3 and 9. In the rectangular microneedle array, if the stretching direction of the skin is not as in FIGS. 3 and 9 but is diagonal, a distance of the microneedle array orthogonal to the stretching direction of the skin is assumed to be L (cm).

The aforementioned phrase "the adhesive layers are aligned with sandwiching the microneedle array" means that the adhesive layers having an adhesive force strong enough to be fixed to the skin with sandwiching the microneedle array are set up. And in the present invention, the direction formed by this adhesive layer and the microneedle array is different from the stretching direction of the skin.

The aforementioned direction different from the stretching direction of the skin is particularly preferably a direction orthogonal to the stretching direction of the skin, but a different angle may be selected as appropriate in accordance with circumstances. Specifically such different angles are appropriately within a range of 45° around an angle of 90°, which is orthogonal to the stretching direction of the skin, for example, preferably within a range of 30°, and more preferably within a range of 15°. Even an angle exceeding 45° around the angle 90° orthogonal to the stretching direction of the skin can be selected depending on the adhesive force of the patch.

Moreover, if the skin is stretched in two directions, for example, it is preferable that the patch is applied so that the adhesive layers with the adhesive force strong enough to be fixed to the skin in an intermediate direction between them are aligned with sandwiching the microneedle array. For example, if the two directions are orthogonal to each other, specifically, the intermediate direction is appropriately within a range from 20° or more to 70° or less in an angle (90°) between the two directions, preferably within a range from 30° or more to 60°, and more preferably 45°. Even an angle out of the range from 20° or more to 70° or less in the angle (90°) between the two directions can be selected depending on the adhesive force of the patch.

Moreover, it may be so constituted that the adhesive force of the adhesive in the direction in which the skin is stretched is weakened so that the adhesive layer does not fix the skin in that direction when the skin shrinks.

A stretching method of the skin is not particularly limited but examples of the methods include a method of stretching by hand, a method of stretching by using an appropriate jig (such as an applicator in FIGS. 10 to 13) which can stretch the skin, a method of stretching with an elastic body such as rubber, a method of stretching by bending a joint in a direction where the skin is stretched, a method of stretching with a thickness of a base of the microneedle array and the like. Moreover, an inserting method of the microneedle array into the skin is not particularly limited but examples of the methods include a method of pressing by hand, a method of insertion by using a spring (a coil-shaped, a plate-shaped, a dome-shaped or the like), and the like (see FIG. 8).

The applying method of the present invention can be applied to humans but can be also applied to the other animals.

In an embodiment, the applying method of the present invention includes a process (A) of stretching the skin, a process (B) of applying a microneedle patch on the stretched skin surface, and a process (C) of releasing the stretching of the skin, and the adhesive force of the adhesive layer satisfies the following Formula (1') in a relationship with a stretching axis in the process (A):

$$S' \times F' < 1.85L' \quad \text{Formula (1')}$$

(in the Formula, S denotes an area ($cm^2$) of a section T not including the microneedle array in the adhesive layer defined by an outer peripheral tangent t of the microneedle array at a right angle to a stretching axis. F denotes an adhesive force (N/cm) per unit of the adhesive layer of the section T. L' denotes a length (cm) in a direction at a right angle to the stretching axis of the microneedle array.)

Hereinafter, the description will be made with referring to the drawings. In FIG. 17, reference numeral 31 denotes a stretching axis in the process (A) of stretching the skin, and $t_1$ and $t_2$ both indicate outer peripheral tangents of the microneedle array 23 forming a right angle to the stretching axis. $T_1$ is a portion of the adhesive layer defined by the tangent $t_1$ and is a section not including the microneedle array. Similarly, $T_2$ is a portion of the adhesive layer defined by the tangent $t_2$ and is a section not including the microneedle array. As illustrated in FIG. 17, when a plurality of the sections T is present, each of the sections satisfies the Formula (1'). L' denotes a length (cm) of the microneedle array in the direction at a right angle to the stretching axis 31 as illustrated in FIG. 18.

In an embodiment, if the patch has a rectangular shape, the microneedle patch can be applied so that a long side of the patch forms a substantially right angle or an angle equivalent to that with respect to the stretching axis. In an embodiment, if the patch has an oval shape, the microneedle patch can be applied so that the long axis of the patch forms a substantially right angle or an angle equivalent to that with respect the stretching axis. In an embodiment, the angle equivalent to the right angle can be 45 to 135°, 60 to 120°, 65 to 115°, 70 to 110°, 72 to 108°, 74 to 106°, 76 to 104°, 78 to 102°, 80 to 100°, 82 to 98°, 84 to 96°, 86 to 94° or 88 to 96°.

2. Patch According to the Present Invention

A microneedle patch according to the present invention (hereinafter referred to as a "patch of the present invention") is to be applied to the skin by stretching and puncturing the skin with the microneedle.

2.1. First Aspect of the Patch of the Present Invention

An example of the patch of the present invention includes the one characterized by: a) the microneedle patch comprises adhesive layers set up in a direction different from directions in which the skin is stretched with sandwiching the microneedle array; and b) there is no adhesive layer on both end portions of the microneedle array in the direction in which the skin is stretched, or even if there is an adhesive layer on the both end portion, a relationship in the following Formula (1) is satisfied:

$$S \times F < 1.85L \quad \text{Formula (1)}$$

(in the Formula, S denotes an area ($cm^2$) of an adhesive layer on the patch sandwiched by an outer peripheral tangent of the microneedle array orthogonal to an axis in which the skin is stretched and an outer periphery of the patch, and if a plurality of such areas is present, it expresses each area. F denotes an adhesive force (N/cm) per unit of the adhesive layer in the direction in which the skin is stretched. L denotes an axial distance (cm) on the dimension of the microneedle array orthogonal to the direction in which the skin is stretched.)

Regardless of the shape of the patch of the present invention, the relationship in the aforementioned Formula (1) is preferably satisfied.

Particularly, in the case of the tetragon adhesive layer and microneedle array as illustrated in FIGS. 3 and 9, the following Formula (2) is preferably satisfied, in which S in the Formula (1) is equal to (a×b):

$$(a\times b)\times F<1.85L \qquad \text{Formula (2)}$$

(in the Formula, a denotes a distance (cm) on the adhesive layer between an outer periphery of the microneedle array orthogonal to the direction in which the skin is stretched and an outer periphery of the adhesive layer, and b denotes an axial distance (cm) orthogonal to the direction of a. F denotes an adhesive force (N/cm) per unit of the adhesive layer in the direction in which the skin is stretched. L denotes an axial distance (cm) on the dimension of the microneedle array orthogonal to the direction in which the skin is stretched.)

Embodiment 1-2 and Embodiment 1-3

The patches of the present invention in the embodiment 1-2 and the embodiment 1-3 have main axes. The main axis is a conceptual axis defined regardless of the shape and the direction of the side of the patch and is an axis in a direction indicated by G in the figures. It may be matched with a direction of a real line indicated by a method of printing on the support or the like.

The patch of the present invention in the embodiment 1-2 is characterized by satisfying the following Formula (3) and/or the following Formula (4):

$$P\times Q<1.85R \qquad \text{Formula (3)}$$

(in the Formula, P denotes an area ($cm^2$) of a section U not including the microneedle array in the adhesive layer defined by an outer peripheral tangent u of the microneedle array. Here, the aforementioned outer peripheral tangent u is in parallel with a main axis. Q denotes an adhesive force (N/cm) per unit of the adhesive layer in the section U. R denotes a length in the microneedle array in the main axis direction.)

$$H\times I>1.85J \qquad \text{Formula (4)}$$

(in the Formula, H denotes an area ($cm^2$) of a section W not including the microneedle array in the adhesive layer defined by an outer peripheral tangent w of the microneedle array. Here, the outer peripheral target w is perpendicular to a main axis. I denotes an adhesive force (N/cm) per unit of the section W. J denotes a length in a direction perpendicular to the main axis.)

Each symbols used in the Formula (3) and the Formula (4) will be described below by referring to the drawings. In FIGS. 19 to 22, reference character G denotes a direction of the main axis. Reference characters $u_1$ and $u_2$ denotes outer peripheral tangents of the microneedle array in parallel with the main axis. Reference characters $w_1$ and $w_2$ denotes outer peripheral tangents of the microneedle array perpendicular to the main axis. Reference character $U_1$ denotes a section of the adhesive layer defined by the tangent $u_1$ and not including the microneedle array. Reference character $U_2$ denotes a section of the adhesive layer defined by the tangent $u_2$ and not including the microneedle array. Reference character $W_1$ denotes a section of the adhesive layer defined by the tangent $w_1$ and not including the microneedle array. Reference character $W_2$ denotes a section of the adhesive layer defined by the tangent $w_2$ and not including the microneedle array.

In the microneedle patch in the embodiment 1-3, a holding time related to the holding force of the adhesive layer in the section U is 120 seconds or less and/or a holding time related to a holding force in the adhesive layer in the section W is 100 seconds or more. The section U indicates a section not including the microneedle array in the adhesive layer defined by the outer peripheral tangent u of the microneedle array in parallel with the main axis as illustrated in FIGS. 19 to 22. The section W indicates a section not including the microneedle array in the adhesive layer defined by the outer peripheral tangent w of the microneedle array perpendicular to the main axis.

The adhesive layer installed on the section W has the holding force (holding time) for a weight of 1 kg measured in accordance with Japanese Industrial Standard (JIS A0237) is 100 seconds or more or 120 seconds or more.

The adhesive layer set up on the section U has the holding force (holding time) for a weight of 1 kg measured in accordance with Japanese Industrial Standard (JIS A0237) is 120 seconds or less, less than 120 seconds or 100 seconds or less.

In an embodiment, the holding time related to the holding force of the adhesive layer in the section U is 120 seconds or less and the holding time related to the holding force of the adhesive layer in the section W is 100 seconds or more.

The patch of the present invention in the embodiment 1-2 and the embodiment 1-3 is to be applied to the skin in the stretched state by stretching the skin and is used to be applied so that the main axis forms a substantially right angle or an angle equivalent to that with respect to the stretching axis. The angle equivalent to the substantially right angle can be 45 to 135°, 60 to 120°, 65 to 115°, 70 to 110°, 72 to 108°, 74 to 106°, 76 to 104°, 78 to 102°, 80 to 100°, 82 to 98°, 84 to 96°, 86 to 94° or 88 to 96°.

If the patch has a rectangular shape, the main axis can be in a direction in parallel with the long side but not limited thereto. If the patch has an oval shape, the main axis can be a direction in parallel with the long axis but not limited thereto.

The angle equivalent to the substantially parallel angle can be ±45°, ±30°, ±25°, ±20°, ±18°, ±16°, ±14°, ±12°, ±10°, ±8°, ±6°, ±4° or ±2° with respect to the direction of the main axis of the patch of the present invention.

2.2. Second Aspect of the Patch of the Present Invention

An example of the patch of the present invention includes the one characterized by that: a) the microneedle patch comprises adhesive layers set up in a direction different from directions in which the skin is stretched with sandwiching the microneedle array; b) a holding time related to a holding force of the adhesive layer on the patch sandwiched by an outer peripheral tangent of the microneedle array in parallel with an axis in which the skin is stretched and an outer periphery of the patch is 100 seconds or more; c) if there is an adhesive layer on both end portions of the microneedle array in the direction in which the skin is stretched, a holding time related to a holding force of the adhesive layer sandwiched by the outer peripheral tangent of the microneedle array orthogonal to the axis in which the skin is stretched and the outer periphery of the patch is less than 120 seconds; and d) in the b) and c), if the sandwiched adhesive layers are present at a plurality of places, a holding time related to a holding force of each of the adhesive layers is 100 seconds or more and less than 120 seconds.

The phrase "holding force of the adhesive layer" is a holding force measured in accordance with Japanese Industrial Standard (JIS Z0237). The patch of the present invention is a patch having an adhesive layer not fixed to the skin in the stretching direction of the skin but fixed in a direction orthogonal to the stretching direction of the skin. As a result, when the skin is stretched and then shrinks again, if the adhesive layer is not fixed to the skin, the patch and therefore the microneedle array are not detached.

That is, it is advantageous that there is substantially no adhesive force of the patch in the stretching direction of the skin. Specifically, in the adhesive layer in the stretching direction of the skin, the holding force (holding time) with respect to a weight of 1 kg in accordance with Japanese Industrial Standard (JIS 20237) is preferably less than 120 seconds or more preferably 100 seconds or less. By such a configuration, the detachment of the microneedle array accompanying the contraction of the skin can be suppressed.

On the other hand, an adhesive force for firmly fixing the microneedle to the skin is required in the direction orthogonal to the stretching direction of the skin. Specifically, in the adhesive layer in the direction orthogonal to the stretching direction of the skin, the holding force (holding time) to a weight of 1 kg in accordance with Japanese Industrial Standard (JIS 20237) is preferably 100 seconds or more or more preferably 120 seconds or more.

The predetermined holding force is adjusted as appropriate depending on a material, a manufacturing condition, a thickness, a dimension and the like of the pressure-sensitive adhesive.

The "direction different from the stretching direction of the skin" is preferably a direction orthogonal to the stretching direction of the skin.

2.3. Third Aspect of the Patch of the Present Invention

An example of the patch of the present invention includes the one to be applied to the skin by stretching and puncturing the skin with the microneedle, characterized by that: a) the patch comprises a rigid flat plate on which a pressure-sensitive adhesive is set up; and b) the microneedle array is set up on the rigid flat plate; or b') the rigid flat plate is raised at a center part to become hollow, and the microneedle array is set up on a plane at the center part of the hollow portion.

The aforementioned "rigid flat plate" refers to a flat plate made of a rigid resin or metal which is not deformed easily, for example. Commercial products can be used as the rigid resin. Specifically, examples include polyethylene, polypropylene, polyvinylchloride, acrylic resin, polyethyleneterephthalate, polystyrene, acrylonitrile-butadiene-styrene copolymer, polycarbonate, polyamide, fluorine resin, polybutyleneterephthalate and the like. Examples of the metal include aluminum, stainless, and titanium.

The rigid flat plate 1 may have a center part 2 raised and hollow as illustrated in FIG. 5. In that case, the microneedle array (a microneedle array portion 3) is internally provided on an inner surface upper part (on a plane of the center part 2) of the hollow portion. Alternatively, the microneedle patch may be internally provided on the inner surface upper part (on the plane of the center part 2) of the hollow portion. Usually, a top surface and/or a side surface of the hollow portion is deformed so that the microneedle array is transferable to the skin side.

The aforementioned "hollow" has an appearance indicted by a symbol 2 in FIG. 5, which is a so-called housing. The hollow can be prepared by heating a pre-extruded film or sheet for softening and then closely attaching it onto a mold for molding (vacuum molding), or alternatively, by injecting a molten resin into a cavity in a metal mold for molding (injection molding, for example). Examples of a material suitable for the aforementioned molding of the hollow (housing) preferably include metal and resins which preferably have resilience and are bent and deformed easily, that is: metal such as aluminum and stainless; and resins such as polyethylene, polypropylene, polyethyleneterephthalate, polystyrene, nylon, acrylic resin, silicon and ABS, for example. When the hollow rigid flat plate and the microneedle are not separated but are held on the skin after the puncturing with the microneedle, it is preferable that the hollow rigid flat plate is not restored to the original form, and metal or a resin which is not restored easily is selected. Alternatively, a mechanism for preventing restoration may be provided separately. Moreover, a thickness of each portion of the housing is selected as appropriate so that desired deformation which will be described later occurs when the housing is pressed from above with a finger.

The "top surface" in the hollow portion refers to a planar portion on the upper part of a raised portion raised upward from a peripheral portion having a flat plate shape forming the hollow (housing). The "side surface" of the hollow portion refers to a side wall portion surrounding the top surface of the raised portion. The skin is fixed by the peripheral portion having the flat plate shape forming a peripheral base portion of the hollow portion.

The top surface and/or the side surface preferably have a fold or an edge for promoting deformation. The "fold or edge" is formed so that, when the top surface portion of the hollow portion 2 is pressed by a finger or the like, the hollow portion 2 is easily deformed and can press down the microneedle array carried inside the top surface to the skin as illustrated in FIG. 5. Moreover, the "fold or edge" is usually set up radially from the top surface to the side surface. Furthermore, the "fold or edge" preferably has features such as symmetrical installation on the side surface so that the top surface can transfer perpendicularly to the skin.

In order to prevent deformation when a non-uniform force is applied to the top surface or the peripheral portion having a flat plate shape by a pressing operation with a finger or the like, a convexoconcave portion for reinforcement may be added in order to increase strength of the top surface and the peripheral portion having a flat plate shape.

The microneedle array portion 3 including the microneedle array may be fixed to the hollow portion 2 by an adhesive or may be physically fixed by fitting using a protrusion or the like. Moreover, a pressure-sensitive adhesive is applied to a skin fixing portion of the rigid flat plate 1. Furthermore, it may be molded integrally with the microneedle array.

When the skin is stretched and then fixed by the rigid flat plate 1, a skin surface of the rigid flat plate 1 is rigid enough not to be deformed easily, and the skin is fixed without contraction. Moreover, in the case of the rigid flat plate 1 with the center part 2 being hollow (each patch in FIG. 5), the top surface and/or the side surface are deformable (particularly (b) to (d) in FIG. 5) so that the top surface advances to the skin surface due to the deformation, and the microneedle can be inserted into the skin.

In the case of the patch of the present invention in the third aspect, the applying direction in the applying method of the present invention is not particularly restraining.

2.4. Others

When the patch of the present invention is to be applied to the skin, the stretching method of the skin is not particularly limited but examples of the methods include a method of stretching by hand, a method of stretching by using an appropriate jig which can stretch the skin, a method of stretching with an elastic body such as rubber, a method of stretching by bending a joint in a direction where the skin is pulled and the like. Moreover, the transferring/inserting method of the microneedle array into the skin is not particularly limited but examples of the methods include a method of pressing by hand, a method of insertion by using a spring (a coil-shaped, a plate-shaped, a dome-shaped or the like), and the like.

The patch of the present invention can be applied to humans but can be also applied to the other animals. Application portions of the patch of the present invention are not particularly limited and in the case of humans, the portions include an inner side or an outer side of a forearm, a back of hand, an inner side or an outer side of an upper arm, a shoulder, a back, a leg, buttocks, a belly, a chest and the like, for example.

Meanings of the other terms according to the patch of the present invention are the same as those above.

3. Assistant Tool According to the Present Invention

An assistant tool according to the present invention (hereinafter referred to as an "assistant tool of the present invention") is an assistant tool for stretching and puncturing the skin with the microneedle and for applying it to the skin and characterized by that: a) the assistant tool comprises a rigid flat plate on which a pressure-sensitive adhesive is set up; b) the rigid flat plate has a ring shape with an opening portion at a center; and c) a size of the opening portion is a size which does not hinder passage of the microneedle array.

The "rigid flat plate" is a ring-shaped rigid flat plate 4 having an opening portion at the center as illustrated in FIG. 6, for example. The shape of the opening portion is not particularly limited and is selected as appropriate in accordance with its strength or puncturing operations by the microneedle array. Examples of the shape include a circle, an oval, a polygon (e.g., a tetragon, a pentagon, a hexagon, an octagon), and the circular and tetragon shapes are preferable among them. Examples of a material include a rigid resin similar to the rigid flat plate and also include metal such as aluminum, stainless, titanium and the like. The rigid flat plate can prevent contraction of the skin by being fixed to the skin surface in a state where the skin is stretched. As a result, the detachment of the applied microneedle array from the skin can be prevented.

By pressure-joining and applying the microneedle array to the skin surface of the opening portion, the microneedle can be inserted into the stretched skin. Specifically, after the skin is stretched with a certain force, the ring-shaped rigid flat plate 4 having an adhesive layer is applied to the skin surface still in the stretched state, the stretched state of the skin is fixed. Then, the microneedle array portion 3 is inserted through the opening portion to the fixed stretched skin (FIG. 6(*g*)). Alternatively, the microneedle array portion 3 is fixed to the ring-shaped rigid flat plate 4 by an adhesive or a fixing jig in advance (FIG. 6(*d*)), the skin is stretched and the stretched state of the skin is kept by applying the ring-shaped rigid flat plate 4 to the skin so as to improve puncturing performance of the microneedle. Then, a pressure is applied to the microneedle array portion 3 or the microneedle array is moved to the skin surface so as to insert the microneedle into the skin.

Moreover, the microneedle array portion 3 and the ring-shaped rigid flat plate 4 may be integrally molded (FIGS. 6(*h*), 6(*i*), and 6(*j*)). In that case, a peripheral portion of the microneedle array is preferably formed by an elastic member so that it can be moved to the skin surface. The elastic member can be selected as appropriate by a material, a shape or a thickness.

When the assistant tool of the present invention is used, the applying direction in the applying method of the present invention is not particularly restraining.

When the assistant tool of the present invention is used, a method of stretching the skin is not particularly limited but examples of the methods include a method of stretching by hand, a method of stretching by using an appropriate jig, a method of stretching with an elastic body such as rubber, a method of stretching by bending a joint in a direction where the skin is pulled. Moreover, a transferring/inserting method of the microneedle array into the skin by using the assistant tool of the present invention is not particularly limited but examples of the methods include a method of pressing by hand, a method of insertion by using a spring (a coil-shaped, a plate-shaped, a dome-shaped or the like), and the like.

The assistant tool of the present invention can be applied to humans but can be also applied to the other animals. Application portions of the assistant tool of the present invention are not particularly limited and in the case of humans, the portions include an inner side or an outer side of a forearm, a back of hand, an inner side or an outer side of an upper arm, a shoulder, a back, a leg, a buttock, a belly, a chest and the like, for example.

Meanings of the other terms related to the assistant tool of the present invention are the same as the above.

4. Device According to the Present Invention

The present invention includes a device of a microneedle array (hereinafter referred to as a "device of the present invention") characterized by comprising the patch of the present invention and an applicator for stretching the skin and transferring/applying the microneedle array to the skin. By means of the applicator according to the device of the present invention, the patch of the present invention (microneedle array) can be effectively applied to the skin. The applicator specifically has a skin stretching mechanism portion 8 for stretching the skin and an applying mechanism portion 9 for transferring and applying the microneedle array to the skin. In the applying mechanism portion 9, a surface on the microneedle array side is preferably as small as possible as long as each microneedle is made to puncture the skin substantially uniformly so that a stress for puncturing with the microneedle can be applied easily. Moreover, inclination is preferably provided on a side surface so that the microneedle array of the microneedle array portion 3 protrudes to the skin surface side (see FIG. 13(*b*) left, for example).

In the device of the present invention, the microneedle array portion 3 including the patch of the present invention is set up so that an adhesive force does not substantially work in a direction in which the skin is stretched. For example, as illustrated in FIG. 10 and FIG. 12(*b*), it is set up with the longitudinal direction of the patch of the present invention being orthogonal to or in an intermediate direction with respect to axial directions in which the skin is stretched (right-and-left direction in FIG. 10(*a*) and FIG. 12 and two directions, that is, up-and-down and right-and-left directions in FIG. 10(*b*)).

The microneedle array portion 3 is usually structurally engaged with to the applicator or the skin stretching mechanism portion 8 by means such as fitting or bonded thereto by an adhesive or the like. In FIG. 12, an installing method of the microneedle array portion 3 to the applicator by the adhesive is illustrated. After the puncturing with the microneedle, the patch of the present invention is usually removed from the applicator and applied to the skin. The adhesive for fixing the patch of the present invention to the applicator is preferably applied on a back side of the patch of the present invention (a surface to which the microneedle does not protrude) and on an inner side from an end portion of the patch of the present invention. As a result, transferring performance of the patch of the present invention to the skin can be improved. This is because, when the patch of the present invention is applied to the skin and is removed from the applicator after the puncturing with the microneedle, a force of peeling-off is largely applied to a farthest end portion of an adhesion portion 10 fixing the patch of the present invention to the skin, and it becomes a trigger point which makes the patch of the present invention easy to be peeled off.

Moreover, the device of the present invention may have a structure in which the microneedle array portion 3 is separated from the skin stretching mechanism portion 8 as illustrated in FIG. 13. In that case, the microneedle array portion 3 is held by another support, and a portion 11 having the microneedle array portion 3 is not directly bonded to or engaged with the applicator or the skin stretching mechanism portion 8. In the device of the present invention with such a structure, the portion 11 having the microneedle array portion 3 is set up without pressure-joining to the skin; alignment is carried out by utilizing shapes of the portion 11 having the microneedle array portion 3 and the skin stretching function portion 8; and the microneedle array is transferred, inserted, and applied to the skin stretched by the skin stretching mechanism portion 8 (see FIG. 14). Examples of the shape of the portion 11 having the microneedle array portion 3 include a notched structure with both ends truncated (see FIG. 13(*a*) right), a structure having cavity portions 12 on the both end portions (see FIG. 13(*b*) right) and the like. Moreover, the alignment may be carried out simply by visual check.

The device of the present invention can be applied to humans but can be also applied to the other animals. Application portions of the patch of the present invention are not particularly limited and in the case of humans, the portions include an inner side or an outer side of a forearm, a back of hand, an inner side or an outer side of an upper arm, a shoulder, a back, a leg, a buttock, a belly, a chest part and the like, for example.

Meanings of the other terms according to the device of the present invention are the same as those above.

EXAMPLES

Here, Examples will be presented to describe the present invention specifically. However, the present invention is not limited to the following Examples at all.

[Example 1] Evaluation Test of Stretching Direction of Skin and Detachment of Microneedle Array (MN)

The skin on the inner side of a forearm was stretched by hand, and the microneedle was inserted together with an adhesive tape for applying (corresponding to a support and an adhesive or an adhesive layer constituting a microneedle patch in a stretched state, and the same applies to the following). After puncturing, the microneedle array was applied to the skin with the adhesive tape. Then the force of stretching the skin was cancelled, and the detachment of the microneedle array and the adhesive tape was visually evaluated.

(1) Shape of Patch: FIG. 4(*a*)

a) Patch of Microneedle Array:

Size of adhesive tape for applying: 30×30 mm

Size of MN: 10×10 mm (A plate having a thickness of 1 mm made of PET was used as a substitute for the microneedle array.)

b) Evaluating Method:

The skin on the inner side of the forearm was stretched to the maximum in a direction orthogonal to the forearm (Stretching rate: 20 to 30%). Then the patch (a) was pressed by a finger, and the adhesive tape was fixed to the skin. The finger was removed from the skin, and whether the skin shrinks, the adhesive tape was detached, and a space was generated between the MN and the skin or not (whether the detachment of the microneedle array was found or not) was visually evaluated.

c) Result:

As shown in Table 1 below, if a material of the adhesive tape was flexible as Million porous tape, it was confirmed that the adhesive tape was detached with the microneedle array as the skin shrank (Test No. 1). On the other hand, if the contraction of the skin could be suppressed, it was confirmed that the microneedle array was not detached (Test No. 2).

TABLE 1

| Test No. | Adhesive tape | Inserting method | Detachment of tape and microneedle |
|---|---|---|---|
| 1 | Million porous tape | press with a finger | Yes |
| 2 | PET film (0.1 mm) + double-sided tape (Nicetack NW) | press with a finger | No |

(2) Shape of Patch: FIG. 4(*b*)

a) Patch of Microneedle Array:

Size of adhesive tape for applying: 30 mmϕ Size of MN: 10×10 mm (A plate having a thickness of 1 mm made of PET was used as a substitute for the microneedle array.)

b) Evaluating Method:

Evaluation was carried out similarly to the aforementioned (1).

c) Result

As shown in Table 2 below, if a material of the adhesive tape was flexible as Million porous tape, it was confirmed that the adhesive tape was detached with the microneedle array as the skin shrank (Test No. 3). On the other hand, if the material of the adhesive tape is rigid and the contraction of the skin could be suppressed, it was confirmed that the microneedle array was not detached (Test Nos. 4, 5).

TABLE 2

| Test No. | Adhesive tape | Inserting method | Detachment of tape and microneedle |
|---|---|---|---|
| 3 | Million porous tape | press with a finger | Yes |
| 4 | PET film (0.1 mm) + double-sided tape (Nicetack NW) | press with a finger | No |
| 5 | rigid plate (polystyrenes 1 mm, 1 mm-thick flange on the outer periphery) + double-sided tape (Nicetack NW) | press with a finger | No (favorable adhesion) |

(3) Shape of Patch: FIG. 4(*c*)

a) Patch of Microneedle Array:

Size of adhesive tape for applying: 10×30 mm

Size of MN: 10×10 mm (A plate having a thickness of 1 mm made of PET was used as a substitute for the microneedle array.)

b) Evaluating Method:

Evaluation was carried out similarly to the aforementioned (1). As a substitute for use of the skin on an inner side of a human forearm, a human skin model was prepared as in a test example 1 which will be described later, and evaluation was carried out also for this human skin model.

c) Result

As shown in Table 3 below, if a material of the adhesive tape was flexible as Million porous tape, it was confirmed that the adhesive tape was detached with the microneedle array as the skin shrank.

TABLE 3

| Test No. | adhesive tape | Evaluating method | Inserting method | Detachment of tape and microneedle |
|---|---|---|---|---|
| 6 | Million porous tape | Human forearm | press with a finger | Yes |
| 7 | Million porous tape | Human skin model | press with a finger | Yes |
| 8 | Million porous tape | Human skin model | ejection by a force of a spring[1)] (0.4 J) | Yes |
| 9 | Million porous tape | Human skin model | ejection by a force of a spring[1)] (1 J) | Yes |

<Note>

J: Joule

[1)]In the case of the ejection by a force of a spring, a compressed coil spring of the assistant tool in FIG. 8 was released at a time so as to give a certain speed to the microneedle array and to cause it to advance into the skin. A workload at that time was set to 0.4 J or 1 J.

(4) Shape of Patch: FIG. 4(*d*)

a) Patch of Microneedle Array:

Size of adhesive tape for applying: 10×30 mm

Size of MN: 10×10 mm (A plate having a thickness of 1 mm made of PET was used as a substitute for the microneedle array.)

b) Evaluating Method:

Evaluation was carried out similarly to (3) of Example 1. The direction of applying the patch is different from the evaluation in the aforementioned (3).

c) Result

As shown in Table 4 below, even if a material of the adhesive tape was flexible as Million porous tape, the microneedle array was not detached with the adhesive tape when the adhesive tape could not substantially exert an adhesive effect.

TABLE 4

| Test No. | Adhesive tape | Evaluating method | Inserting method | Detachment of tape and microneedle |
|---|---|---|---|---|
| 10 | Million porous tape | Human forearm | press with a finger | No (favorable) |
| 11 | Million porous tape | Human skin model | press with a finger | No (favorable)[1)] |
| 12 | Million porous tape | Human skin model | ejection by a force of a spring[2)] (0.4 J) | No (favorable)[1)] |

TABLE 4-continued

| Test No. | Adhesive tape | Evaluating method | Inserting method | Detachment of tape and microneedle |
|---|---|---|---|---|
| 13 | Million porous tape | Human skin model | ejection by a force of a spring[2)] (1 J) | No (favorable)[1)] |

<Note>

J: Joule

[1)]In order to confirm presence of the Detachment of the adhesive tape and the microneedle, it was confirmed that the microneedle (array) used for the puncturing was not detached from the skin not only by visual evaluation but also by obtaining an X-ray micro CT image (see FIG. 7).

[2)]The ejection was performed by the force of the spring by using an assistant tool in FIG. 8 which was the same as that in Table 3.

[Example 2] Evaluation of Maximum Adhesive Force in Skin Stretching Direction In order to prepare a patch in which the adhesive force of the patch does not substantially work in the stretching direction of the skin and thus the patch is not pulled corresponding to the contraction of the skin, an upper limit of the adhesive force (allowable maximum adhesive force) in the skin stretching direction was estimated.

(1) Equipment

Patch Containing Microneedle Array:

The patch was prepared by fixing a resin plate of 10×10 mm×1 mmh to a commercial surgical tape as a substitute for the microneedle array.

Commercial Surgical Tape:

1538 by 3M Company (adhesive force: 3.7 N/cm), 1527 by 3M Company (adhesive force: 2.8 N/cm), 1525 by 3M Company (adhesive force: 1.7 N/cm)

The values of the adhesive forces are adhesive forces of the adhesive tape with a width of 2.5 cm with respect to a steel plate (catalog values).

(2) Method

The skin of the human forearm was stretched by a hand, and a patch containing a resin plate of 10×10 mm×1 mmh or a resin plate with 20×20×1 mmh was pressed and applied to the stretched skin with a force of 20N using a jig having a diameter of 5 mm.

The patch was fixed by a fixing surgical tape (approximately 5 mm× approximately 30 mm) in a direction orthogonal to the skin stretching direction as illustrated in FIG. 9.

After the fixation, stretching of the skin was released, and presence of the detachment of the microneedle array after contraction was observed.

(3) Result

As shown in Table 5 below, when a distance (cm) in an axial direction orthogonal to the direction in which the skin was stretched in the dimension of the microneedle was 1 cm, the detachment of the microneedle array did not occur if a fixing force between the adhesive tape and the skin was less than 1.85 N.

TABLE 5

| Test No. | Tape name | Adhesive force F (N/cm) | Size a (cm) | Size b (cm) | Size L (cm) | Fixing force for skin (N) | Evaluation (Presence of the detachment) |
|---|---|---|---|---|---|---|---|
| 14 | 1538 by 3M | 3.7 | 0.75 | 1 | 1 | 2.78 | x |
| 15 | 1538 | 3.7 | 0.5 | 1 | 1 | 1.85 | x |
| 16 | 1538 | 3.7 | 0.4 | 1 | 1 | 1.48 | ○ |

TABLE 5-continued

| Test No. | Tape name | Adhesive force F (N/cm) | Size a (cm) | Size b (cm) | Size L (cm) | Fixing force for skin (N) | Evaluation (Presence of the detachment) |
|---|---|---|---|---|---|---|---|
| 17 | 1538 | 3.7 | 0.4 | 2 | 2 | 2.96 | ○ |
| 18 | 1538 | 3.7 | 0.5 | 2 | 2 | 3.70 | Δ |
| 19 | 1538 | 3.7 | 1.5 | 2 | 2 | 11.1 | x |
| 20 | 1527 | 2.8 | 1 | 1 | 1 | 2.8 | x |
| 21 | 1527 | 2.8 | 0.68 | 1 | 1 | 1.90 | Δ |
| 22 | 1527 | 2.8 | 0.54 | 1 | 1 | 1.51 | ○ |
| 23 | 1527 | 2.8 | 0.54 | 2 | 2 | 3.02 | ○ |
| 24 | 1538 | 3.7 | 1.2 | 1.2 | 1 | 5.33 | x |
| 25 | 1527 | 2.8 | 1.2 | 1.2 | 1 | 4.03 | x |

<Note>
Circle: No detachment of MN and favorable,
Triangle: Slight detachment of MN,
Cross: Defective with detachment of MN
When L = 1 cm, the size of the microneedle is 1 cm × 1 cm
When L = 2 cm, the size of the microneedle is 2 cm × 2 cm From the aforementioned results and the like, it was found that, assuming that the adhesive force of the adhesive tape to the skin is F (N/cm), the following relational Formula (1) was completed:

$$S \times F < 1.85L \quad \text{Formula (1)}$$

(in the Formula, S denotes an area ($cm^2$) of an adhesive layer on the patch sandwiched by an outer peripheral tangent of the microneedle array orthogonal to an axis in which the skin is stretched and an outer periphery of the patch, and if a plurality of such areas is present, it expresses each area. F denotes an adhesive force (N/cm) per unit of the adhesive layer in the direction in which the skin is stretched. L denotes an axial distance (cm) on the dimension of the microneedle array orthogonal to the direction in which the skin is stretched.)

As the patch according to the experiment in Table 5, the relational formula in the case where the adhesive layer and the microneedle array have tetragon shapes can be expressed as the following Formula (2) in which S in the relational Formula (1) is equal to (a×b):

$$(a \times b) \times F < 1.85L \quad \text{Formula (2)}$$

(in the Formula, a denotes a distance (cm) on the adhesive layer between an outer periphery of the microneedle array orthogonal to the direction in which the skin is stretched and an outer periphery of the adhesive layer, and b denotes an axial distance (cm) orthogonal to the direction of a. F denotes an adhesive force (N/cm) per unit of the adhesive layer in the direction in which the skin is stretched. L denotes an axial distance (cm) on the dimension of the microneedle array orthogonal to the direction in which the skin is stretched.)

As a result, by selecting the adhesive force and the shape of the patch so as to satisfy the aforementioned Formula (1) or (2), the detachment of the adhesive tape and the microneedle array after application to the skin can be avoided because of the result of the Table 5. Moreover, the optimal adhesive force of the adhesive tape can also be selected in accordance with the size of the microneedle array.

[Example 3] Evaluation of Adhesive Layer which can be Set Up in Skin Stretching Direction Since the upper limit of the adhesive force (allowable maximum adhesive force) in the skin stretching direction could be evaluated in Example 2, the case where the patch illustrated in FIG. 3 was applied was then verified.

a) Patch of Microneedle Array:

Adhesive tape for applying: Surgical tape 1538 by 3M Company

Size of adhesive tape for applying: (10+2a)×30 mm

Size of microneedle array: 10×10 mm (a plate having a thickness of 1 mm made of PET was used as a substitute for the microneedle array). Therefore, b is 1 mm.

b) Evaluating Method:

Three types of adhesive tapes, that is, a=b+2 mm, b+4 mm, b+9 mm were prepared as the adhesive tapes for applying, the skin on the inner side of the human forearm was stretched, the three types of the patches in Table 6 were applied, and a degree of adhesion (co-movability with the skin) was evaluated.

c) Result:

As shown in Table 6, it was indicted that if a was 5 mm or less, the tape was not co-moved with the skin, and the microneedle was not detached.

TABLE 6

| Test No. | Distance of a (mm) | | Detachment of tape and microneedle |
|---|---|---|---|
| 26 | b + 2 | 3 | No |
| 27 | b + 4 | 5 | No |
| 28 | b + 9 | 10 | Yes |

As a result, it was shown that if the distance of a satisfies the following formula, the adhesive tape was not co-moved with the contraction of the skin so that the microneedle was not detached from the skin:

$$a < b + 4$$

[Example 4] Patch of Microneedle Array Having Rigid Flat Plate on Skin Adhesion Surface for Suppression of Contraction of Stretched Skin As Test No. 5 in Example 1, when the rigid flat plate is used, the contraction of the skin can be prevented so that the microneedle array can be favorably maintained in close contact with the skin.

Thus, the patch or the assistant tool in which a part carrying the microneedle array was made hollow and only a part for puncturing the skin was made free from contact with the flat plate was prepared and evaluated.

(1) Patch Carrying Microneedle Array with Part for Puncturing Skin being Hollow:

The patch carrying the microneedle array with a part for puncturing the skin being hollow as illustrated in FIG. 5 was prepared.

The patch having a form in which the microneedle array and a fixing tape (the microneedle portion 3) were internally mounted and an adhesive layer was mounted on the skin surface side of the rigid flat plate 1 was set up on the stretched skin. The skin surface was fixed by the rigid flat plate 1, the deformable top surface and/or side surface were deformed so as to puncture the skin with the microneedle. Furthermore, pressing was performed so as to apply the microneedle array and the adhesive tape to the skin.

(2) Assistant Tool for Fixing Stretched Skin, Puncturing it with Microneedle and then Fixing the Microneedle The assistant tool for puncturing with the microneedle array having a skin-puncturing portion with the shape illustrated in FIG. 6 being an opening portion was prepared.

By the method described in Example 1, the periphery of puncturing portion of the microneedle array was fixed onto the stretched skin with the assistant tool, and the microneedle array was pressed and applied to the opening portion.

[Example 5] Holding Force Test of Adhesive Tape

Evaluation was made in accordance with Japanese Industrial standard (JIS Z0237). The test piece satisfied the following conditions:

(1) Test Piece: Width 10 mm and Length 150 mm; Width 12 mm and Length 150 mm; Width 20 mm and Length 150 mm The test was conducted for those with Test Nos. 16, 17, 22, 23, 24, and 25 of Example 2.

(2) Test Plate

Stainless plate (125 mm×50 mm)

(3) Method

A part of a test piece having a predetermined width (b) and a predetermined length (a) was placed at a center of one end of the test plate without applying a pressure.

Subsequently, a roller (the one prescribed in Pressure device 10.2.4, Japanese Industrial Standard) was reciprocated twice on the test piece at a speed of 10±0.5 mm/s so as to crimp the test piece and the test plate.

One end of the test plate was fixed within 1 minute after the crimping so that the test plate and the test piece were suspended perpendicularly, and a weight of 1 kg was attached to an end portion folded of the test piece.

Elapsed time (holding time) from attachment of the weight until the test piece was completely peeled off the test plate was measured.

(4) Result

TABLE 7

| Test No. | Test No. of Example 2 | Tape name | Adhesive force (N/cm) | Size a (cm) | Size b (cm) | Holding time (second) | Evaluation of example 2 |
|---|---|---|---|---|---|---|---|
| 29 | 16 | 1538 | 3.7 | 0.4 | 1 | 30 | ○ |
| 30 | 22 | 1527 | 2.8 | 0.54 | 1 | 50 | ○ |
| 31 | 17 | 1538 | 3.7 | 0.4 | 2 | 70 | ○ |
| 32 | 23 | 1527 | 2.8 | 0.54 | 2 | 100 | ○ |
| 33 | 24 | 1538 | 3.7 | 1.2 | 1.2 | 170 | x |
| 34 | 25 | 1527 | 2.8 | 1.2 | 1.2 | 120 | x |

○: No detachment of MN
x: detachment of MN

In a state where the microneedle array is fixed in the stretching direction of the skin, when the skin is stretched and then shrinks again, the tape adhesive layer applied to the skin in the stretching direction of the skin is pushed up and correspondingly the microneedle array is also detached so that an administration effect of a drug and the like is reduced. However, if the tape adhesive layer is not fixed when the skin shrinks, the tape adhesive layer and therefore the microneedle array are not detached.

That is, it is advantageous that there is substantially no adhesive force of the patch in the stretching direction of the skin. Specifically, from the aforementioned results, if the holding force (holding time) with respect to the weight of 1 kg is less than 120 seconds or preferably 100 seconds or less, the microneedle array cannot be detached easily corresponding to the contraction of the skin.

On the other hand, an adhesive force for firmly fixing the microneedle to the skin is required for the tape adhesive layer in the direction orthogonal to the stretching direction of the skin. Specifically, from the aforementioned result, a condition can be cited that does not cause the detachment of the microneedle array, that is, the holding force (holding time) with respect to the weight of 1 kg being 100 seconds or more or preferably 120 seconds or more. The direction different from the stretching direction of the skin is preferably a direction orthogonal to the stretching direction of the skin.

Actually, in order to satisfy the predetermined holding force, the holding force is adjusted depending on a material, a manufacturing condition, a thickness, a dimension and the like.

[Test Example 1] Puncturing Performance Test Using Human Skin Model (1) Construction of Human Skin Model Skin removed from a human belly was mounted on an upper surface of a silicon sheet with hardness of 5 degrees.

(2) Puncturing Method

The aforementioned human skin model was stretched with a stretching rate of 20 to 50%, and the microneedle array was inserted together with the applying tape by hand with a stress of 20 N. Alternatively, insertion was performed by using a spring with a workload of 0.4 Joule.

(3) Shape of Patch: (c) and (d) in FIG. 4

Size of tape for applying: 10×30 mm

Size of MN: 10×10 mm (A plate having a thickness of 1 mm made of PET was used as a substitute for the microneedle array.)

(4) Result

As shown in Table 8 below, with the human skin model, the detachment of the adhesive tape can be avoided by using the applying method in FIG. 4(*d*), and removal of the microneedle array from the skin together with the adhesive tape could be avoided. On the other hand, with the applying method in FIG. 4(*c*), the detachment of the adhesive tape and the PET plate, which is a substitute for the microneedle array, was found.

TABLE 8

| Test No. | Adhesive tape | Evaluating method | Inserting method | Detachment of tape |
|---|---|---|---|---|
| 25 | Million porous tape applying method shown in FIG. 4(c) | Human skin model | press with a finger (20N) | Yes |
| 26 | Million porous tape applying method shown in FIG. 4(d) | Human skin model | press with a finger (20N) | No (favorable) |
| 27 | Million porous tape applying method shown in FIG. 4(c) | Human skin model | ejection by a force of a spring[1)] (0.4 J) | Yes |
| 28 | Million porous tape applying method shown in FIG. 4(d) | Human skin model | ejection by a force of a spring[1)] (0.4 J) | No (favorable) |

<Note>
J: Joule
[1)]In the ejection by the force of the spring, the jig in FIG. 8 was used so that a compressed coil spring was released at a time so as to give a certain speed to the microneedle array and to cause it to advance into the skin, to pressurize the human skin model and to apply the patch.

[Test Example 2] Evaluation of Adhesion of Microneedle Array to Skin by X-Ray Micro CT (1) Equipment X-Ray Micro CT:

TDM1000H-II (2K) by Yamato Scientific Co., Ltd., Set tube voltage: 90 kV, set tube current: 0.032 mA, photographing field size: approximately 11 mm, scan time: approximately 17 minutes, slice thickness: 20 μm Microneedle Array:

Microneedle array made of polyglycolic acid resin (length 600 μm, interval 800 μm, 120 pieces) of approximately 1 $cm^2$ was used.

(2) Method

The skin was stretched by 10 to 20% by using the microneedle array, and it was installed by a double-sided tape. The human skin model of the test example 1 was used, the applying method of the adhesive tape was in accordance with FIG. 4(*d*), and the skin was pressed with the force of 10 N for approximately 10 seconds.

Then a peripheral portion of the pressed microneedle array was bonded to the human skin model with an instantaneous adhesive.

The skin on which the microneedle was bonded was taken out, installed in the micro CT device, and a three-dimensional CT image was measured.

(3) Result

As a measurement result, a three-dimensional CT image as illustrated in FIG. 7 was obtained. As illustrated in FIG. 7, it was found that approximately ⅔ of the microneedle was inserted into the skin, and the detachment of the microneedle array from the skin was not observed.

INDUSTRIAL APPLICABILITY

The applying method of the present invention and the patch of the present invention that can be used for the method or the assistant tool of the present invention or the device of the present invention improve puncturing performance of the microneedle, can firmly fix the microneedle array to the skin, and can administer the drug quantitatively without waste. Therefore, they are useful as a pharmaceutical product or the like.

EXPLANATION OF SYMBOLS

1 Rigid flat plate
2 Hollow portion
3 Microneedle array portion
4 Ring-shaped rigid flat plate
5 Coil spring
6 Fixing surgical tape
7 Fixing surgical tape in skin stretching direction
8 Skin stretching mechanism portion
9 Applying mechanism portion
10 Adhesion portion
11 Portion having the microneedle array portion
12 Cavity portion
21 Support
22 Adhesive layer (pressure-sensitive adhesive)
23 Microneedle array

What is claimed is:

1. A method of applying a microneedle patch comprising adhesive layers and a microneedle array including a microneedle, comprising:

stretching skin with a tension using a hand, an appropriate jig or an elastic body, applying, while the skin is stretched, the microneedle patch to the skin in a direction in which an adhesive force of the patch does not substantially work, whereby lifting-up of the patch from the skin is prevented.

2. The method of applying a microneedle patch according to claim 1, wherein:

a) the adhesive layers are not present on both end portions of the patch in the direction in which the skin is stretched, or even if there are the adhesive layers on the both end portions, the adhesive layers on the both end portions have no adhesive force strong enough to be fixed to the skin; and b) the adhesive layers having the adhesive force strong enough to be fixed to the skin in a direction different from the direction in which the skin is stretched, wherein the microneedle array is sandwiched between the adhesive layers which are aligned in a different direction in which the skin is stretched.

3. The method of applying a microneedle patch according to claim 2, wherein having no adhesive force strong enough to be fixed to the skin is to satisfy a relationship in the following Formula (1):

$$S \times F < 1.85L \text{ . . . Formula} \qquad (1);$$

wherein S denotes an area ($cm^2$) of an adhesive layer on the patch sandwiched by an outer peripheral tangent of the microneedle array orthogonal to an axis in which the skin is stretched and an outer periphery of the patch, and if a plurality of such areas are present, it expresses each area, and S is not 0;

F denotes an adhesive force (N/cm) per unit of the adhesive layer in the direction in which the skin is stretched; and L denotes an axial distance (cm) on the dimension of the microneedle array orthogonal to the direction in which the skin is stretched.

4. The method of applying a microneedle patch according to claim 3, wherein the planar shapes of the adhesive layer and the microneedle array are a tetragon, and, in Formula (1), S is (a×b) as shown in the following Formula (2):

$$(a \times b) \times F < 1.85L \text{ . . . Formula} \qquad (2);$$

wherein a denotes a distance (cm) on the adhesive layer between an outer periphery of the microneedle array orthogonal to the direction in which the skin is stretched and an outer periphery of the adhesive layer, and b denotes an axial distance (cm) orthogonal to the direction of a;

F denotes an adhesive force (N/cm) per unit of the adhesive layer in the direction in which the skin is stretched; and L denotes an axial distance (cm) on the dimension of the microneedle array orthogonal to the direction in which the skin is stretched.

5. The method of applying a microneedle patch according to claim 3, wherein a planar shape of at least one of the patch, the adhesive layer and the microneedle array is a polygon, a tetragon, a circle or an oval.

6. The method of applying a microneedle patch according to claim 5, wherein the planar shapes of the adhesive layer and the microneedle array are a tetragon, and, Formula (1), S is (a×b) as shown in the following Formula (2):

$$(a \times b) \times F < 1.85L \text{ . . . Formula} \qquad (2);$$

wherein a denotes a distance (cm) on the adhesive layer between an outer periphery of the microneedle array orthogonal to the direction in which the skin is stretched and an outer periphery of the adhesive layer, and b denotes an axial distance (cm) orthogonal to the direction of a;

F denotes an adhesive force (N/cm) per unit of the adhesive layer in the direction the skin is stretched; and L denotes an axial distance (cm) on the dimension of the microneedle array orthogonal to the direction in which the skin is stretched.

7. The method of applying a microneedle patch according to claim 2, wherein a planar shape of at least one of the patch, the adhesive layer and the microneedle array is a polygon, a tetragon, a circle or an oval.

8. The method of applying a microneedle patch according to claim 7, wherein the planar shapes of the adhesive layer and the microneedle array are a tetragon, and, in Formula (1), S is (a×b) as shown in the following Formula (2):

$$(a \times b) \times F < 1.85L \ldots \text{Formula} \quad (2);$$

wherein a denotes a distance (cm) on the adhesive layer between an outer periphery of the microneedle array orthogonal to the direction in which the skin is stretched and an outer periphery of the adhesive layer, and b denotes an axial distance (cm) orthogonal to the direction of a;

F denotes an adhesive force (N/cm) per unit of the adhesive layer in the direction the skin is stretched; and L denotes an axial distance (cm) on the dimension of the microneedle array orthogonal to the direction in which the skin is stretched.

9. The method of applying a microneedle patch according to claim 1, wherein a planar shape of at least one of the patch, the adhesive layer and the microneedle array is a polygon, a tetragon, a circle or an oval.

10. A microneedle patch applied to a skin by stretching and puncturing the skin with a microneedle, wherein:

the microneedle patch comprises adhesive layers and a microneedle array comprising the microneedle, a) the microneedle patch comprises the adhesive layers set up in a direction different from directions in which the skin is stretched, the microneedle array is sandwiched between the adhesive layers which are aligned in a different direction from the direction in which the skin is stretched; and b) there is no adhesive layer on both end portions of the microneedle array in the direction in which the skin is stretched, or even if there is an adhesive layer on the both end portion, a relationship in the following Formula (1) is satisfied:

$$S \times F < 1.85L \ldots \text{Formula} \quad (1);$$

wherein S denotes an area ($cm^2$) of an adhesive layer on the patch sandwiched by an outer peripheral tangent of the microneedle array orthogonal to an axis in which the skin is stretched and an outer periphery of the patch, and if a plurality of such areas are present, it expresses each area, and S is not 0;

F denotes an adhesive force (N/cm) per unit of the adhesive layer in the direction in which the skin is stretched; and L denotes an axial distance (cm) on the dimension of the microneedle array orthogonal to the direction in which the skin is stretched.

11. The microneedle patch according to claim 10, wherein a planar shape of at least one of the patch, the adhesive layer and the microneedle array is a polygon, a tetragon, a circle or an oval.

12. The microneedle patch according to claim 11, wherein the planar shapes of the adhesive layer and the microneedle array are a tetragon, and, in Formula (1), S is (a×b) as shown in the following Formula (2):

$$(a \times b) \times F < 1.85L \ldots \text{Formula} \quad (2);$$

wherein a denotes a distance (cm) on the adhesive layer between an outer periphery of the microneedle array orthogonal to the direction in which the skin is stretched and an outer periphery of the adhesive layer, and b denotes an axial distance (cm) orthogonal to the direction of a;

F denotes an adhesive force (N/cm) per unit of the adhesive layer in the direction in which the skin is stretched; and L denotes an axial distance (cm) on the dimension of the microneedle array orthogonal to the direction in which the skin is stretched.

13. A microneedle patch applied to a skin by stretching and puncturing the skin with a microneedle, wherein:

a) the microneedle patch comprises: adhesive layers set up in a direction different from directions in which the skin is stretched; the microneedle array is sandwiched between the adhesive layers; and an adhesive layer on both end portions of the microneedle array in the direction in which the skin is stretched;

b) a holding time related to a holding force of the adhesive layer on the patch sandwiched between an outer peripheral tangent of the microneedle array in parallel with an axis in which the skin is stretched and an outer periphery of the patch is 100 seconds or more;

c) a holding time related to a holding force of the adhesive layer sandwiched between the outer peripheral tangent of the microneedle array orthogonal to the axis in which the skin is stretched and the outer periphery of the patch is less than 120 seconds; and d) in the b) and c), if the sandwiched adhesive layers are present at a plurality of places, a holding time related to a holding force of each of the adhesive layers is respectively 100 seconds or more and less than 120 seconds.

14. The microneedle patch according to claim 13, wherein the holding time related to the holding force of the adhesive layer sandwiched between the outer peripheral tangent of the microneedle array in parallel with the axis in which the skin is stretched and the outer periphery of the patch is 120 seconds or more.

15. The microneedle patch according to claim 14, wherein the holding time related to the holding force of the adhesive layer sandwiched between the outer peripheral tangent of the microneedle array orthogonal to the axis the skin is stretched and the outer periphery of the patch is 100 seconds or less.

16. The microneedle patch according to claim 13, wherein the holding time related to the holding force of the adhesive layer sandwiched between the outer peripheral tangent of the microneedle array orthogonal to the axis the skin is stretched and the outer periphery of the patch is 100 seconds or less.

* * * * *